(12) United States Patent
McFadden et al.

(10) Patent No.: US 8,227,440 B2
(45) Date of Patent: *Jul. 24, 2012

(54) USE OF MYXOMA VIRUS FOR THE THERAPEUTIC TREATMENT OF CANCER AND CHRONIC VIRAL INFECTION

(75) Inventors: Grant McFadden, Gainesville, FL (US); John C. Bell, Ottawa (CA)

(73) Assignee: Robarts Research Institute, London (CA)

(*) Notice: Subject to any disclaimer, the term of this patent is extended or adjusted under 35 U.S.C. 154(b) by 75 days.

This patent is subject to a terminal disclaimer.

(21) Appl. No.: 12/549,939
(22) Filed: Aug. 28, 2009
(65) Prior Publication Data

US 2009/0317362 A1 Dec. 24, 2009

Related U.S. Application Data

(63) Continuation of application No. 10/547,859, filed as application No. PCT/CA2004/000341 on Mar. 8, 2004, now Pat. No. 7,582,614.

(60) Provisional application No. 60/452,521, filed on Mar. 7, 2003, provisional application No. 60/455,393, filed on Mar. 18, 2003.

(51) Int. Cl.
*A61K 48/00* (2006.01)
*A01N 65/00* (2009.01)

(52) U.S. Cl. .......................... 514/44; 424/93.1; 424/93.2
(58) Field of Classification Search .................. None
See application file for complete search history.

(56) References Cited

U.S. PATENT DOCUMENTS 4,806,347 A 2/1989 Leibowitz

FOREIGN PATENT DOCUMENTS

| EP | 0 972 840 | 1/2000 |
|---|---|---|
| WO | 96/03997 | 2/1996 |
| WO | 97/26904 | 9/1997 |
| WO | 99/04026 | 1/1999 |
| WO | 99/18799 | 4/1999 |
| WO | 00/62735 | 10/2000 |
| WO | 01/04318 | 1/2001 |
| WO | 2007/143545 | 12/2007 |

OTHER PUBLICATIONS

Bertagnoli et al. J Virol 1996;70:5061-6.*
Fenner, FEMS Microbiol Rev 2000;24:123-33.*
Liu et al. J Virol 2011;85:3270-82.*
McCabe et al. Vaccine 2002;20:2454-62.*
Cameron, et al., "The Complete DNA Sequence of Myxoma Virus", Virology, 264: 298-318, 1999.
Matin, et al., "Impaired x-Interferon Signaling in Transitional Cell Carcinoma: Lack of p48 Expression in 5637 Cells", Cancer Research, 61: 2261-2266, Mar. 2001.
Balachandra, et al., "Defective Translational Control Facilitates Vesicular Stomatitis Virus Oncolysis", Cancer Cell, 5: 51-65, Jan. 2004.
Sun, et al., Interferon-x Resistance in a Cutaneous T-Cell Lymphoma Cell Line is Associated with Lack of STAT1 Expression, Blood, 91(2): 570-576, Jan. 1998.
Wong, et al., "Interferon-resistant Human Melanoma Cells are Deficient in ISGF3 Components, STAT1, STAT2, and p48-ISGFy*", The Journal of Biological Chemistry, 272(45): 28779-28785, Nov. 1997.
Stojdl, et al., "VSV Strains with Defects in their Ability to Shutdown Innate Immunity are potent Systemic Anti-Cancer Agents", Cancer Cell, 4: 263-275, Oct. 2003.
Strong, et al., "The v-erbB Oncogene Confers Enhanced Cellular Susceptibility to Reovirus Infection", Journal of Virology, 70(1). 612-618, Jan. 1996.
Nemunaitis, et al., Phase II Trial of Intratumoral Administration of ONXY-015, a Replication-Selective Adenovirus, in Patients with Refractory Head and Neck Cancer, Journal of Clinical Oncology, 19(2): 289-298, Jan. 2001.
Kerr, et al., "Immune Responses to Myoxma Virus", Viral Immunology, 15(2): 229-246, Jul. 2002.
Lalani, et al., "Role of the Myxoma Virus Soluble CC-Chemokine Inhibitor Glycoprotein, M-T1, during Myxoma Virus Pathogenesis", Virology, 256: 233-245, 1999.
Barcena, et al., "Isolation of an attenuated myxoma virus field strain that can confer protection against myxomatosis on contacts of vaccinates". Arch Virol, 146: 759-771, 2000.
Sypula, et al., "Myxoma Virus Tropism is Human Tumor Cells", Gene Therapy and Molecular Biology, 8: 103-114, Apr. 2004.
Lun, et al., "Myxoma Virus is a Novel Oncolytic Virus with Significant Antitumor Activity against Experimental Human Gliomas", Cancer Res. 65(21): 9982-9990, 2005.
Barrett; et al; "Immunomodulatory Proteins of Myxoma Virus", Seminars in Immunology, 13: 73-84, 2001.
Kim. et al. "Replication-selective Virotherapy for Cancer: Biological Principles, Risk Management and Future Direction", Nature Medicine, 7(7): 781-787, 2001.
Thome, et al., "Future Directions for the Field of Oncolytic Virotherapy: A Perspective on the use of Vaccinia Virus", Expert Opin. Biol. Ther., 4(8): 1307-1321, Aug. 2004.
Thome, et al., "Vaccinia Virus and Oncolytic Virotherapy of Cancer", Current Opinion in Molecular Therapeutics, 7(4) pp. 359-365, 2005.
Thome, et al., "The Use of Oncolytic Vaccinia Viruses in the Treatment of Cancer: A New Role for an Old Ally?", Current Gene Therapy, 5: 429-443, 2005. McFadden, "Poxvirus Tropism", Natural Reviews Microbiology, 3: 201-213, 2005.
Shen, et al., "Fighting Cancer with Vaccinia Virus: Teaching New Tricks to an Old Dog", Molecular Therapy, 11(2): 160-195, 2095.
Taber's Cyclopedic Medical Dictionary, 20th ed. (Philadelphia: F.A. Davis, 2005), p. 1423.
Mossman, et al., "Myxoma Virus M-T7, a Secreted Homolog of the Interferon-y Receptor, Is a Critical Virulence Factor for the Development of Myxomatosis in European Rabbits", Virology, 215: 17-30 1996.
Vile, et al., "The Oncolytic virotherapy treatment platform for cancer: Unique biological and biosafety points to consider", Cancer Gene Therapy, 9:1062-1067, Dec. 2002.
Robinson, et al., "Progress towards using recombinant myxoma virus as a vector for fertility control in rabbits", Reprod. Fertil. Dev., 9:77-83, 1997.
Barcena, et al., "Horizontal Transmissible Protection against Myxomatosis and Rabbit Hemorrhagic Disease by Using a Recombinant Myxoma Virus", Journal of Virology, 74(3): 1114-1123, 2000.
Best, et al., "Coevolution of Host and Virus: Cellular Localization of Virus in Myxoma Virus Infection of Resistant Susceptible European Rabbits", Virology, 277: 76-91, 2000.
Green, et al., "Adenoviral vectors: Systemic delivery and tumor targeting", Cancer Gene Therapy, 9: 1036-1042, Dec. 2002.
Katze et al. "Viruses and interferon: A fight for supremacy" Nat. Rev. Immunol (Sep. 2002) 2:675-687.

* cited by examiner

*Primary Examiner* — Q. Janice Li
(74) *Attorney, Agent, or Firm* — Douglas A. Golightly

(57) ABSTRACT

The present invention relates to therapeutic use of Myxoma virus. Myxomas virus can selectively infect cells that have a deficient innate anti-viral response, including cells that are not responsive to interferon and can be used to treat diseases characterized by the presence of such cells, including cancer.

15 Claims, 24 Drawing Sheets

| Nonpermissive WT MEFs | Anti-IFNα/β (200 U/ml) | Anti-IFNα/β (2000 U/ml) | Anti-IFNγ (200,000 U/ml) |

Mock Neutralization

**Anti-IFNα/β
(2000 u/ml)**

STAT1 Y701 phosphorylation

STAT1 S727 phosphorylation

STAT1 protein 0  6  12 24 36 48

Hours postinfection

USE OF MYXOMA VIRUS FOR THE THERAPEUTIC TREATMENT OF CANCER AND CHRONIC VIRAL INFECTION

FIELD OF THE INVENTION

The present invention relates generally to therapeutic use of Myxoma virus.

BACKGROUND OF THE INVENTION

Current treatments used to treat various types of cancer tend to work by poisoning or killing the cancerous cell. Unfortunately, treatments that are toxic to cancer cells typically tend to be toxic to healthy cells as well. Moreover, the heterogenous nature of tumours is one of the primary reasons that effective treatments for cancer remain elusive. Current mainstream therapies such as chemotherapy and radiotherapy tend to be used within a narrow therapeutic window of toxicity. These types of therapies are considered blunt tools that have limited applicability due to the varying types of tumour cells and the limited window in which these treatments can be administered.

Modern anticancer therapies currently being developed attempt to selectively target tumour cells while being less toxic to healthy cells, thereby being more likely to leave healthy cells unaffected.

Oncolytic viral therapy is one approach that aims to exploit cellular differences between tumour cells and normal cells. This therapy uses replication-competent, tumour-selective viral vectors as anti-cancer agents. The oncolytic virus either specifically targets cancer cells for infection, or is more suited for efficient replication in cancer cells versus healthy cells. These replication-competent, oncolytic viruses are either naturally occurring or genetically engineered to be a highly selective and highly potent means of targeting the heterogeneous tumour population. Since the replication selective oncolytic virus does not replicate efficiently in normal cells, toxicity to the patient should be low, particularly in comparison to traditional therapies such as radiation or chemotherapy.

Numerous studies have reported oncolytic activity for various virus strains, with the most promising oncolytic viruses being a naturally occurring or genetically modified version of adenovirus, herpes simplex virus 1 ("HSV1"), Reovirus, Vaccinia Virus, Vesicular Stomatitis Virus ("VSV") or Poliovirus. Modified oncolytic viruses currently under investigation as anticancer agents include HSV, adenovirus, Newcastle disease virus ("NDV"), Reovirus and Vaccinia virus, measles, VSV and poliovirus. Various oncolytic viruses are in Phase I and Phase II clinical trials with some showing sustained efficacy. However, it is unknown which viruses will best fulfill the oncolytic goals of sustained replication, specificity and potent lytic activity. A completely efficient candidate for an oncolytic viral vector would be one that has a short lifecycle, forms mature virions quickly, spreads efficiently from cell to cell and has a large genome ready for insertions. As well, evidence suggests that inhibiting the early innate immune response and slowing the development of Th1 responses are important for the efficacy of oncolytic therapy. It is clear that human viruses are highly immunogenic, as measured by the high level of antibody and T cell responses that are observed in the normal population for many of the viruses being considered for the development of oncolytic viruses.

Clinical work has shown that current oncolytic viruses are indeed safe, but are not potent enough as monotherapies to be completely clinically effective. As insufficient or inefficient infection of tumour cells is usually observed, the current movement is to arm candidate viruses by genetically engineering them to express therapeutic transgene to increase their efficiency. Most of the above-mentioned oncolytic viruses are also being tested in combination with other common oncolytic therapies.

Adenovirus can be easily genetically manipulated and has well-known associated viral protein function. In addition, it is associated with a fairly mild disease. The ONYX-015 human adenovirus (Onyx Pharmaceuticals Inc.) is a one of the most extensively tested oncolytic viruses that has been optimized for clinical use. It is believed to replicate preferentially in p53-negative tumours and shows potential in clinical trials with head and neck cancer patients. However, reports show that ONYX-015 has only produced an objective clinical response in 14% of treated patients (Nemunaitis J, Khuri F, Ganly I, Arseneau J, Posner M, Vokes E, Kuhn J, McCarty T, Landers S, Blackburn A, Romel L, Randlev B, Kaye S, Kirn D. *J. Clin. Oncol.* 2001 Jan. 15; 19(2):289-98).

WO96/03997 and WO97/26904 describe a mutant oncolytic HSV that inhibits tumour cell growth and is specific to neuronal cells. Further advantages are that the HSV can be genetically modified with ease and drugs exist to shut off any unwanted viral replication. However, the application of such a common human pathogen is limited, as it is likely that the general population has been exposed and acquired an immune response to this virus, which would attenuate the lytic effect of the virus. HSV can also cause serious side effects or a potentially fatal disease.

Reovirus type III is associated with relatively mild diseases and its viral gene function is fairly well understood. Reovirus type III is currently being developed by Oncolytic Biotech as a cancer therapeutic which exhibits enhanced replication properties in cells expressing mutant ras oncogen and preferentially grows in PKR−/− cells (Strong J. E. and P. W. Lee, *J. Virology*, 1996. 70:612-616). However, Reovirus is difficult to genetically manipulate and its viral replication cannot be easily shut off.

VSV is associated with relatively mild diseases and also has well-known viral gene function. WO99/04026 discloses the use of VSV as a vector in gene therapy for the expression of wide treatment of a variety of disorders. However, VSV suffers from the same problems as the Reovirus in that it is difficult to genetically manipulate and its viral replication cannot be easily shut off.

Vaccina virus and Poliovirus are other candidate oncolytic viruses described in the art but have been associated with a serious or potentially fatal disease.

U.S. Pat. No. 4,806,347 discloses the use of gamma interferon and a fragment of IFNγ against human tumour cells. WO99/18799 discloses a method of treating disease in a mammal in which the diseased cells have defects in an interferon-mediated antiviral response, comprising administering to the mammal a therapeutically effective amount of an interferon-sensitive, replication competent clonal virus. It specifically discloses that VSV particles have toxic activity against tumour cells but that alleviation of cytotoxicity in normal cells by VSV occurs in the presence of interferon. WO99/18799 also discloses that NDV-induced sensitivity was observed with the interferon-treated tumour cells but that adding interferon to normal cells makes these cells resistant to NDV. This method aims to make cells sensitive to interferon by infecting them with interferon sensitive viruses.

SUMMARY OF THE INVENTION

In one aspect, the present invention provides a method for inhibiting a cell that has a deficient innate anti-viral response comprising administering to the cell an effective amount of Myxoma virus.

In one aspect, the invention provides a method for treating a disease state characterized by the presence of cells that have a deficient innate anti-viral response, comprising administering to a patient in need thereof an effective amount of Myxoma virus.

The present invention further provides use of an effective amount of Myxoma virus for inhibiting a cell that has a deficient innate anti-viral response and in the manufacture of a medicament for inhibiting a cell that has a deficient innate anti-viral response.

The present invention further provides use of an effective amount of Myxoma virus for treating a disease state in a patient, wherein the disease state is characterized by the presence of cells that have a deficient innate anti-viral response and in the manufacture of a medicament for treating such a disease state in a patient In another aspect, the present invention provides a pharmaceutical composition comprising Myxoma virus and a pharmaceutically acceptable carrier for use in inhibiting a cell that has a deficient innate anti-viral response and for use in treating a disease state characterized by the presence of cells that have a deficient innate anti-viral response.

In another aspect, the present invention provides a kit comprising Myxoma virus and instructions for inhibiting a cell that has a deficient innate anti-viral response or for treating a disease state characterized by the presence of cells that have a deficient innate anti-viral response. The disease states includes cancer and a chronic viral infection.

The present invention further provides a method for detecting a cell that has a deficient innate anti-viral response in a patient, comprising administering to the patient a Myxoma virus modified to express a detectable marker; allowing the virus to infect a cell that has a deficient innate anti-viral response in the patient; and detecting the cell expressing the detectable marker in the patient.

The present invention further provides a method for detecting in a sample a cell that has a deficient innate anti-viral response, comprising culturing the cell, exposing cultured cells to Myxoma virus; and determining infectivity of cells by Myxoma virus.

The present invention is based on the unexpected discovery that rabbit Myxoma virus can selectively infect cells, including human tumour cells, that have a deficient innate anti-viral response, including those that are non-responsive to interferon. The term "innate" as used in this context describes non-antigen specific immune response. Since myxoma virus does not replicate efficiently in normal human cells, the virus can therefore be used as a treatment for various disorders and conditions characterized by cells that have a deficient innate anti-viral response, including cells that are non-responsive to interferon, for example, as an oncolytic treatment for cancer. The virus can also be used to identify cells that have a deficient innate anti-viral response and to image these cells in vivo.

Other aspects and features of the present invention will become apparent to those of ordinary skill in the art upon review of the following description of specific embodiments of the invention in conjunction with the accompanying figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

In the figures, which illustrate embodiments of the present invention, by way of example only.

DETAILED DESCRIPTION

Figure 1:
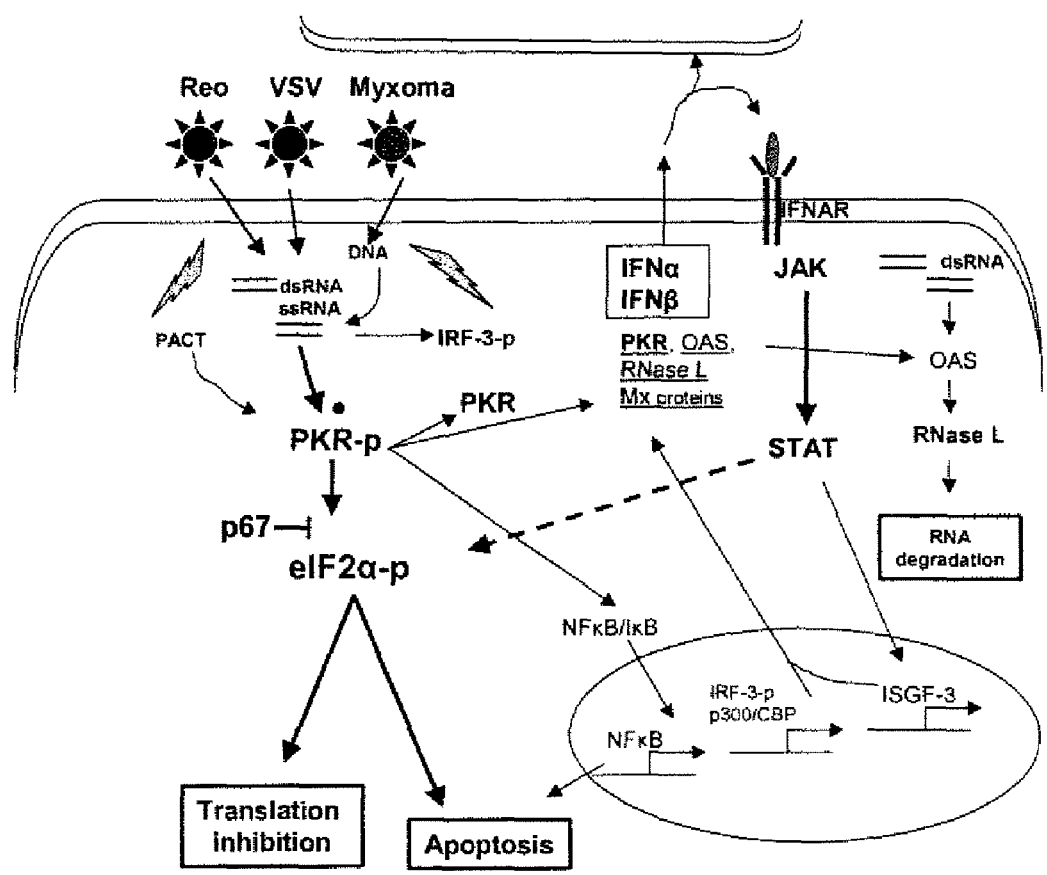
FIG. 1 is a schematic diagram of interferon mediated antiviral signalling scheme induced upon viral infection of a cell.

The inventors have discovered that Myxoma virus, a virus that normally infects rabbits, can selectively infect and kill cells including human cells that have a deficient innate anti-viral response, for example, cells that are non-responsive to interferon. Myxoma virus, on the other hand, does not replicate efficiently in normal human cells. Since many diseases or conditions are characterized by the presence of cells that have a deficient innate anti-viral response, including cells that are not responsive to interferon, for example, cancer, Myxoma virus can be used to treat such diseases and conditions, including cancer, with low toxicity for normal healthy cells.

Myxoma virus can also be used to treat chronically infected cells as such cells have a deficient innate anti-viral response. For example, many viruses encode gene products that function to inhibit the antiviral, interferon response of cells. Myxoma virus can selectively infect these cells.

Myxoma Virus ("MV") is the causative agent of myxomatosis in rabbits. MV belongs to the Leporipoxvirus genus of the Poxyiridae family, the largest of the DNA viruses. MV induces a benign disease in its natural host, the Sylvilagus rabbit in the Americas. However, it is a virulent and host-specific poxvirus that causes a fatal disease in European rabbits, characterized by lesions found systemically and especially around the mucosal areas. (Cameron C, Hota-Mitchell S, Chen L, Barrett J, Cao J X, Macaulay C, Willer D, Evans D, McFadden G. *Virology* 1999, 264(2): 298-318; Kerr P & McFadden G. *Viral Immunology* 2002, 15(2): 229-246).

MV is a large virus with a double-stranded DNA genome of 163 kb which replicates in the cytoplasm of infected cells (B. N. Fields, D. M. Knipe, P. M. Howley, Eds., *Virology* Lippincott Raven Press, New York, 2nd ed., 1996). MV is known to encode a variety of cell-associated and secreted proteins that have been implicated in down-regulation of the host's immune and inflammatory responses and inhibition of apoptosis of virus-infected cells. MV can be taken up by all human somatic cells. However, other than in normal somatic rabbit cells, if the cells have a normal innate anti-viral response, the virus will not be able to productively infect the cell, meaning the virus will not be able to replicate and cause cell death.

Interferons ("IFNs") are a family of cytokines that are secreted in response to a variety of stimuli. Interferons bind to cell surface receptors, activating a signaling cascade that leads to numerous cellular responses, including an anti-viral response and induction of growth inhibition and/or apoptotic signals. Interferons are classified as either type I or type II. Type I IFNs include IFN-α, -β, -τ, and -ω, which are all monomeric; the only type II IFN is IFN-γ, a dimer. Twelve different subtypes of IFN-α are produced by 14 genes, but all other IFNs are monogenic (Arduini et al., 1999). IFNs exert direct anti-tumour activity via the modulation of oncogene expression. Overexpression of growth-stimulating oncogenes or loss of tumour suppressor oncogenes can lead to malignant transformation. Some oncogenes implicated in the genesis of cancer are p53, Rb, PC, NF1, WT1, DCC.

Myxoma virus, as well as other oncolytic viruses such as Reovirus and VSV, needs to bypass the anti-viral defenses that exist in normal healthy cells in order to be able to replicate within cells. MV and other oncolytic viruses induce interferon production, and are generally sensitive to the anti-viral effect of the IFN pathway. Relevant proteins induced by the IFN anti-viral response, and which principally affect virus multiplication include PKR, OAS synthetase and Rnase L nuclease. PKR activates eIF2α, leading to inhibition of translation and induction of apoptosis. A schematic representation of the IFN response pathway is depicted in FIG. 1. In normal cells, MV is directly affected by PKR and eIF2α.

Anti-viral response pathways are often disrupted in cancerous cells. For example, reduced or defective response to IFN is a genetic defect that often arises during the process of transformation and tumour evolution. Over 80% of tumour cell lines do not respond to, or exhibit impaired responses to, interferon. (Stojdl et al., *Cancer Cell* (2003) 4: 263-275 and references cited therein; Wong et al. *J Biol. Chem.* (1997) 272(45):28779-85; Sun et al. *Blood.* (1998) 91(2):570-6; Matin et al. *Cancer Res.* (2001) 61(5):2261-6; Balachandran et al *Cancer Cell* (2004) 5(1):51-65). The inventors have surprisingly discovered that MV can infect and kill cancer cells, including human tumour cells, and without being limited by any particular theory, it is believed that MV can infect these cells because they have a deficient innate anti-viral response.

Evidence suggests that inhibiting the early innate immune response and slowing the development of Th1 responses are important for the efficacy of oncolytic therapy. Although Myxoma virus is a virulent virus, it is host-specific and has a very narrow host range; it does not infect humans or mice. Without being limited by any specific theory, it is believed that since Myxoma virus is a non-human virus, it should encounter no pre-existing immune recognition in humans. Therefore, its potential as an oncolytic virus will be less compromised and Myxoma virus should provide more potent infection of permissive tumour cells than native human viruses, thereby can provide an effective oncolytic treatment for cancer.

Thus, in one embodiment, there is provided a method for inhibiting a cell that has a deficient innate anti-viral response comprising administering to the cell an effective amount of Myxoma virus. In one embodiment, the cell is non-responsive to interferon.

In specific embodiments, the cell is a mammalian cancer cell. In one embodiment the cell is a human cancer cell including a human solid tumour cell.

In another embodiment, the cell is chronically infected with a virus.

The term "a cell that has a deficient innate anti-viral response" as used herein refers to a cell that, when exposed to a virus or when invaded by a virus, does not induce anti-viral defence mechanisms, which include inhibition of viral replication, production of interferon, induction of the interferon response pathway, and apoptosis, which may or may not be mediated by interferon, and is thereby infectable by MV. The term includes a cell that has a reduced or defective innate anti-viral response upon exposure to or infection by a virus as compared to a normal cell, for example, a non-infected, or non-cancer cell. This includes a cell that is non-responsive to interferon and a cell that has a reduced or defective apoptotic response or induction of the apoptotic pathway. The deficiency may be caused by various causes, including infection, genetic defect, or environmental stress. It will however be understood that when the deficiency is caused by a pre-existing infection, superinfection by MV may be excluded and a skilled person can readily identify such instances. A skilled person can readily determine without undue experimentation whether any given cell type has a deficient innate anti-viral response and therefore infectable by Myxoma virus. For example, VSV is commonly used to measure an anti-viral response of a cell.

To assess whether a given cell type, for example a given cancer cell type, has a deficient innate anti-viral response, a skilled person can take an explant, grow some of the cells in vitro and determine infectability by VSV or alternatively, by Myxoma.

The term "a cell that is non-responsive to interferon" as used throughout the specification means a cell that does not respond to the activity of interferon, for example anti-viral or anti-tumour activity of interferon or that has an abnormal interferon response, for example, a reduced or ineffective response to interferon, or abnormal interferon signalling as measured by, for example, phosphorylation or activation of signalling molecules such as transcription factors, for example STAT1. For example, without limitation, the cell may not undergo inhibition of proliferation or it may not be killed when exposed to interferon levels sufficient to induce such a response in a cell that is responsive to interferon. The cell that is non-responsive to interferon may have a defect in the intracellular signalling pathway or pathways that are normally activated in the responsive cells. Typically, susceptibility to infection by VSV is indicative of non-responsiveness to interferon, and a skilled person can readily determine whether a particular cell is non-responsive to interferon by its ability, or lack thereof, to inhibit VSV infection in the presence of interferon or using other markers of interferon activity known in the art, for example, the level of expression of IFN stimulated genes such as PKR, STAT, OAS, MX.

The term "replication-competent" as used throughout the specification refers to a virus that is capable of infecting and replicating within a particular host cell.

The term "a cell" as used herein includes a single cell as well as a plurality or population of cells. Administering an agent to a cell includes both in vitro and in vivo administrations.

The term "effective amount" as used herein means an amount effective, at dosages and for periods of time necessary to achieve the desired result.

The term "animal" as used herein includes all members of the animal kingdom, including humans.

The term "inhibiting" a cell that has a deficient innate anti-viral response includes cell death by lysis or apoptosis or other mechanisms of cell death, in addition to rendering the cell incapable of growing or dividing.

The Myxoma virus may be any virus that belongs to the Leporipoxvirus species of pox viruses that is replication-competent. The Myxoma virus may be a wild-type strain of Myxoma virus or it may be a genetically modified strain of Myxoma virus.

The Myxoma virus genome may be readily modified to express one or more therapeutic transgenes using standard molecular biology techniques known to a skilled person, and described for example in Sambrook et al. ((2001) Molecular Cloning: a Laboratory Manual, $3^{rd}$ ed., Cold Spring Harbour Laboratory Press). A skilled person will be able to readily determine which portions of the Myxoma viral genome can be deleted such that the virus is still capable of productive infection. For example, non-essential regions of the viral genome that can be deleted can be deduced from comparing the published viral genome sequence with the genomes of other well-characterized viruses (see for example C. Cameron, S. Hota-Mitchell, L. Chen, J. Barrett, J.-X. Cao, C. Macaulay, D. Willer, D. Evans, and G. McFadden, *Virology* (1999) 264: 298-318)).

The term "therapeutic gene" or "therapeutic transgenes" as used herein is intended to describe broadly any gene the expression of which effects a desired result, for example, anti-cancer effect. For example, the virus may be modified to carry a gene that will enhance the anticancer effect of the viral treatment. Such a gene may be a gene that is involved in triggering apoptosis, or is involved in targeting the infected cell for immune destruction, such as a gene that repairs a lack of response to interferon, or that results in the expression of a cell surface marker that stimulates an antibody response, such as a bacterial cell surface antigen. The virus may also be modified to express genes involved in shutting off the neoplastic or cancer cell's proliferation and growth, thereby preventing the cells from dividing. As well, the virus may be modified to include therapeutic genes, such as genes involved in the synthesis of chemotherapeutic agents, or it may be modified to have increased replication levels in cells of the particular species from which the cells to be inhibited or killed are derived, for example, human cells. Specific examples of genes that may be inserted into the Myxoma virus to increase its anticancer effect include the human gene for the TRAK protein or the adenoviral gene that encodes the E4 orf4 polypeptide, both of which proteins are involved in killing human tumour cells.

It will be understood that therapeutic effect of the Myxomas virus may be achieved by cell lysis by the virus or by delivery of therapeutic products.

The virus may be prepared using standard techniques known in the art. For example, the virus may be prepared by infecting cultured rabbit cells with the Myxoma virus strain that is to be used, allowing the infection to progress such that the virus replicates in the cultured cells and can be released by standard methods known in the art for disrupting the cell surface and thereby releasing the virus particles for harvesting. Once harvested, the virus titre may be determined by infecting a confluent lawn of rabbit cells and performing a plaque assay (see Mossman et al. (1996) *Virology* 215:17-30).

In one embodiment, there is provided a method for treating a disease state characterized by the presence of cells that have a deficient innate anti-viral response in a patient in need of such treatment comprising administering to the patient an effective amount of Myxoma virus. The patient may be any animal, including a mammal, including a human.

"A disease state characterized by the presence of cells that have a deficient innate anti-viral response" as used herein refers to any disease, disorder or condition which is associated with, related to, or a characteristic of which is the presence of cells that have a deficient innate anti-viral response and which disease, disorder, condition or symptoms thereof may be treated by killing these cells. For example, the disease state may be cancer. The disease state may also include chronic infection with a virus.

"Treating" a disease state refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total), whether detectable or undetectable. "Treating" can also mean prolonging survival of a patient beyond that expected in the absence of treatment. "Treating" can also mean inhibiting the progression of disease, slowing the progression of disease temporarily, although more preferably, it involves halting the progression of the disease permanently. As will be understood by a skilled person, results may not be beneficial or desirable if, while improving a specific disease state, the treatment results in adverse effects on the patient treated that outweigh any benefits effected by the treatment.

In one embodiment, the disease state is cancer. The cancer may be any type of cancer wherein at least some of the cells, although not necessarily all of the cells have a deficient innate anti-viral response. In one embodiment, the cancer may be a cancer wherein at least some of the cells are non-responsive to interferon. As used herein, the terms "tumour", "tumour cells", "cancer" and "cancer cells", (used interchangeably) refer to cells that exhibit abnormal growth, characterized by a significant loss of control of cell proliferation or cells that have been immortalized. The term "cancer" or "tumour" includes metastatic as well as non-metastatic cancer or tumours. As used herein, "neoplastic" or "neoplasm" broadly refers to a cell or cells that proliferate without normal growth inhibition mechanisms, and therefore includes benign tumours, in addition to cancer as well as dysplastic or hyperplastic cells.

A cancer may be diagnosed using criteria generally accepted in the art, including the presence of a malignant tumor.

Types of cancer that may be treated according to the present invention include, but are not limited to, hematopoietic cell cancers including leukemias and lymphomas, colon cancer, lung cancer, kidney cancer, pancreas cancer, endometrial cancer, thyroid cancer, oral cancer, ovarian cancer, laryngeal cancer, hepatocellular cancer, bile duct cancer, squamous cell carcinoma, prostate cancer, breast cancer, cervical cancer, colorectal cancer, melanomas and any other tumours. Solid tumours such as sarcomas and carcinomas include but are not limited to fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In another embodiment, the disease state is a chronic viral infection.

The chronically infecting virus may be any virus that infects and replicates in cells of an animal in a persistent manner over a prolonged period so as to cause a pathological condition. The chronically infecting virus may be a virus that is associated or correlated with the development of cancer.

A chronic infection with a virus may be diagnosed using standard methods known in the art. For example, a chronic viral infection may be detected by the presence of anti-viral antibodies in the patient or a positive test for the presence of viral RNA or DNA in cells of the patient.

The virus may be administered to the patient using standard methods of administration. In one embodiment, the virus is administered systemically. In another embodiment, the virus is administered by injection at the disease site. In a particular embodiment, the disease state is a solid tumour and the virus is administered by injection at the tumour site. In various embodiments, the virus may be administered orally or parenterally, or by any standard method known in the art.

When administered to a patient, an effective amount of the virus is the amount required, at the dosages and for sufficient time period, to alleviate, improve, mitigate, ameliorate, stabilize, prevent the spread of, slow or delay the progression of or cure the disease. For example, it may be an amount sufficient to achieve the effect of reducing the number or destroying cancerous cells or neoplastic cells or reducing the number of or destroying cells chronically infected with a virus, or inhibiting the growth and/or proliferation of such cells.

The effective amount to be administered to a patient can vary depending on many factors such as the pharmacodynamic properties of the virus, the mode of administration, the age, health and weight of the patient, the nature and extent of the disease state, the frequency of the treatment and the type of concurrent treatment, if any, and the virulence and titre of the virus.

One of skill in the art can determine the appropriate amount based on the above factors. The virus may be administered initially in a suitable amount that may be adjusted as required, depending on the clinical response of the patient. The effective amount of virus can be determined empirically and depend on the maximal amount of the virus that can be administered safely, and the minimal amount of the virus that produces the desired result.

To produce the same clinical effect when administering the virus systemically as that achieved through injection of the virus at the disease site, administration of significantly higher amounts of virus may be required. However, the appropriate dose level should be the minimum amount that would achieve the desired result.

The concentration of virus to be administered will vary depending on the virulence of the particular strain of Myxoma that is to be administered and on the nature of the cells that are being targeted. In one embodiment, a dose of less than about $10^9$ plaque forming units ("pfu") is administered to a human patient. In various embodiments, between about $10^2$ to about $10^9$ pfu, between about $10^2$ to about $10^7$ pfu, between about $10^3$ to about $10^6$ pfu, or between about $10^4$ to about $10^5$ pfu may be administered in a single dose.

Effective amounts of virus can be given repeatedly, depending upon the effect of the initial treatment regimen. Administrations are typically given periodically, while monitoring any response. It will be recognized by a skilled person that lower or higher dosages than those indicated above may be given, according to the administration schedules and routes selected.

The virus may be administered alone or in combination with other therapies, including chemotherapy, radiation therapy or other anti-viral therapies. For example, the virus may be administered either prior to or following surgical removal of a primary tumour or prior to, concurrently with or following treatment such as administration of radiotherapy or conventional chemotherapeutic drugs. In one embodiment, the virus can be administered in combination with, or in a sequential fashion with, other oncolytic viruses, which may demonstrate specificity for varying tumour cell types.

To aid in administration, the virus may be formulated as an ingredient in a pharmaceutical composition. Therefore, in a further embodiment, there is provided a pharmaceutical composition comprising Myxoma virus and a pharmaceutically acceptable diluent. The invention in one aspect therefore also includes such pharmaceutical compositions for use in inhibiting a cell that has a deficient innate anti-viral response or treating a disease state characterized by the presence of cells that have a deficient innate anti-viral response. The compositions may routinely contain pharmaceutically acceptable concentrations of salt, buffering agents, preservatives and various compatible carriers. For all forms of delivery, the recombinant virus may be formulated in a physiological salt solution.

The pharmaceutical compositions may additionally contain other therapeutic agents, such as anti-cancer agents. In one embodiment, the compositions include a chemotherapeutic agent. The chemotherapeutic agent, for example, may be substantially any agent which exhibits an oncolytic effect against cancer cells or neoplastic cells of the patient and that does not inhibit or diminish the tumour killing effect of the virus. For example, the chemotherapeutic agent may be, without limitation, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent is one that is known to be effective against the particular cell type that is cancerous or neoplastic.

The proportion and identity of the pharmaceutically acceptable diluent is determined by chosen route of administration, compatibility with a live virus and standard pharmaceutical practice. Generally, the pharmaceutical composition will be formulated with components that will not significantly impair the biological properties of the live virus.

The pharmaceutical composition can be prepared by known methods for the preparation of pharmaceutically acceptable compositions suitable for administration to patients, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the virus in association with one or more pharmaceutically acceptable vehicles or diluents, and contained in buffer solutions with a suitable pH and iso-osmotic with physiological fluids.

The pharmaceutical composition may be administered to a patient in a variety of forms depending on the selected route of administration, as will be understood by those skilled in the art. The composition of the invention may be administered orally or parenterally. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

The pharmaceutical composition may be administered orally, for example, with an inert diluent or with an assimilable carrier, or it may be enclosed in hard or soft shell gelatin capsules, or it may be compressed into tablets. For oral therapeutic administration, the virus may be incorporated with an excipient and be used in the form of ingestible tablets, buccal tablets, troches, capsules, elixirs, suspensions, syrups, wafers and the like.

Solutions of the virus may be prepared in a physiologically suitable buffer. Under ordinary conditions of storage and use, these preparations contain a preservative to prevent the growth of microorganisms, but that will not inactivate the live virus. A person skilled in the art would know how to prepare suitable formulations. Conventional procedures and ingredients for the selection and preparation of suitable formulations are described, for example, in Remington's Pharmaceutical Sciences and in The United States Pharmacopeia The National Formulary (USP 24 NF19) published in 1999.

In different embodiments, the composition is administered by injection (subcuteanously, intravenously, intramuscularly, etc.) directly at the disease site, such as a tumour site, or by oral administration, alternatively by transdermal administration.

The forms of the pharmaceutical composition suitable for injectable use include sterile aqueous solutions or dispersion and sterile powders for the extemporaneous preparation of sterile injectable solutions or dispersions, wherein the term sterile does not extend to the live Myxoma virus itself that is to be administered. In all cases the form must be sterile and must be fluid to the extent that easy syringability exists.

The dose of the pharmaceutical composition that is to be used depends on the particular condition being treated, the severity of the condition, the individual patient parameters including age, physical condition, size and weight, the duration of the treatment, the nature of concurrent therapy (if any), the specific route of administration and other similar factors that are within the knowledge and expertise of the health practitioner. These factors are known to those of skill in the art and can be addressed with minimal routine experimentation.

The Myxoma virus, or pharmaceutical compositions comprising the Myxoma virus may also be packaged as a kit, containing instructions for use of the virus, including the use of Myxoma virus to inhibit a cell that has a deficient innate anti-viral response, or use of Myxoma virus to treat a disease state characterized by the presence of cells that have a deficient innate anti-viral response, in a patient in need thereof. The disease state may be cancer, or it may be a chronic viral infection.

The present invention also contemplates the use of Myxoma virus for inhibiting a cell that has a deficient innate anti-viral response. In one embodiment, the cell is non-responsive to interferon. There is further provided use of Myxoma virus for treating a disease state characterized by the presence of cells that have a deficient innate anti-viral response, in a patient in need thereof. In one embodiment the disease state is cancer. There is also provided use of Myxoma virus in the manufacture of a medicament, for inhibiting a cell that has a deficient innate anti-viral response, or for treating a disease state characterized by the presence of cells that have a deficient innate anti-viral response in a patient in need thereof.

The ability of MV to selectively infect cells that have a deficient innate anti-viral response in animals other than its natural host provides for the use of MV in detecting cells in the animal that have a deficient innate anti-viral response, including cells that are non-responsive to interferon. Such cells may otherwise not be easily detectable, for example certain cancer cells that have not yet advanced to palpable tumour, or have not yet induced noticeable symptoms in the animal.

Thus, in one embodiment, there is provided a method for detecting cells that have a deficient innate anti-viral response in a patient, comprising administering to the patient a Myxoma virus modified to express a detectable marker; allowing the virus to infect a cell that has a deficient innate anti-viral response in the patient; and detecting the cell expressing the detectable marker in the patient.

The infected cells may be detected using any conventional method for visualizing diagnostic images. The method of detection will depend on the particular detectable marker that is used. For example, cells infected with Myxoma virus genetically modified to express a fluorescent protein may be detected using fluorescence digital imaging microscopy. Other methods include computed tomography (CT), whole body scan such as position emission tomography (PET), magnetic resonance imaging (MRI), and sonography. Skilled artisans will be able to determine the appropriate method for detecting a particular detectable marker.

The detectable marker includes, but is not limited to, any marker for which genes for its expression or synthesis can be inserted into the Myxoma genome so as to result in expression or synthesis of the marker within cells that are infected by the modified virus. For example, in one embodiment, the detectable marker may be a fluorescent protein. The infected cells may be detected at a suitable time interval after administration of the modified virus to the patient, so as to allow for the virus to infect any cells that have a deficient innate anti-viral response, and to express the detectable marker in such cells at levels that would allow for detection. For example, detection may occur anywhere between 2 and 20 days following administration to the patient of the virus genetically modified to express a fluorescent protein.

The detecting method may be carried out repeatedly at intervals in a patient in order to monitor the presence of cells that have a deficient innate anti-viral response in that patient. For example, the method for detecting such cells using Myxoma virus may be carried out on a patient at 6 month, 1 year or 2 year intervals, as is necessary, depending on the nature of the cells that has a deficient innate anti-viral response and the nature of any disease state caused as a result of the presence of such cells in a patient. Repeating the method over a time period allows for monitoring of the progression or remission of disease state, or the spread of disease within the body of the patient.

Myxoma virus is capable of selectively infecting cells that have a deficient innate anti-viral response, and can be used as an indicator of such a deficiency in cells. Thus, cells removed from a patient may be assayed for deficiency in innate anti-viral response using the methods of the present invention. Such determination may indicate, when combined with other indicators, that the patient may be suffering from a particular disease state, for example, cancer.

In one embodiment therefore, there is provided a method for detecting in a sample a cell that has a deficient innate anti-viral response comprising culturing the cell, exposing cultured cells to Myxoma virus; and determining infectivity of cells by Myxoma virus The cells may be removed from a subject, including a human subject using known biopsy methods. The biopsy method will depend on the location and type of cell that is to be tested.

Cells are cultured according to known culturing techniques, and are exposed to MV by adding live virus to the culture medium. The multiplicity of infection ("MOI") may be varied to determine an optimum MOI for a given cell type, density and culture technique, using a positive control cell culture that is known to be infected upon exposure to MV.

Infectivity of the cultured cells by MV may be determined by various methods known to a skilled person, including the ability of the MV to cause cell death. It may also involve the addition of reagents to the cell culture to complete an enzymatic or chemical reaction with a viral expression product. The viral expression product may be expressed from a reporter gene that has been inserted into the MV genome.

In one embodiment the MV may be modified to enhance the ease of detection of infection state. For example, the MV may be genetically modified to express a marker that can be readily detected by phase contrast microscopy, fluorescence microscopy or by radioimaging. The marker may be an expressed fluorescent protein or an expressed enzyme that may be involved in a colorimetric or radiolabelling reaction. In another embodiment the marker may be a gene product that interrupts or inhibits a particular function of the cells being tested.

All reference cited herein are fully incorporated by reference.

EXAMPLES

Virus Strains

Viral strains used include wildtype MV, MV modified to express either green fluorescence protein ("GFP") or β-galactosidase ("LacZ"), and killed ("dead") MV. Viruses were prepped and titred using standard techniques.

Cell Strains

Mouse experiments were performed using mouse embryo fibroblasts ("MEFs") derived from a wild-type mouse, and from the following mouse knockouts: IFNα/β receptor homozygous knockout; STAT1 homozygous knockout; PKR heterozygous; RNaseL heterozygous knockout; Mx1 heterozygous knockout; triple PKR/RNaseL/Mx1 homozygous knockout.

Human experiments were performed on BGMK control cells and human tumour cell lines HT29, HOP92, OVCAR4, OVCAR5, SK-MEL3, SK-MEL28, M14, SKOV3, PC3, DU145, CAKI-1, 786-0, T47D, MDAMB 435, SF04, U87, A172, U373, Daoy and D384 as described in Stojdl et al., *Cancer Cell* (2003) 4: 263-275.

Methods

Generally, assays and experiments were performed as described in Lalani et al. *Virology* (1999) 256: 233-245 and Johnston et al. *J Virology* (2003) 77(13): 7682-7688.

For the in vivo mouse studies, nude mice were implanted with intracranial human gliomas U87. 15 days after implantation, mice were intratumourally injected with live or dead MV GFP, at a titre of $5 \times 10^6$, or mock-infected. 72 hours post-infection, animals were sacrificed, the brains removed, embedded in OCT (Optimal Cutting Temperature compound), and frozen sections were cut. Myxoma-GFP was visualized in whole brain sections by fluorescence microscopy. Sections were then fixed and stained with H&E (hemotoxylin and eosin) to visualize the tumor.

For human tumour cell assays, the tumours were trypsonized and plated immediately after surgery and infected with virus the next day at an MOI of 0.1, 1.0 or 10. Data was gathered regarding cytotoxicity and viral expression using phase microscopy and fluorescent microscopy, respectively, at 24 and 48 hours post-infection. Assays using the yellow tetrazolium salt MTT were performed to quantify the % cell survival (as a percentage of cells surviving mock infection) at 48, 72 or 96 hours post-infection.

Human pediatric medulloblastoma cell lines, Daoy and D384, were infected with 10 M.O.I. of Myxoma-GFP. 72 hours after infection, cell viability was measured using MTT.

Infections of Mouse Cell Lines

Previous research showed that some clones of mouse 3T3 cells transfected with chemokine receptors were infectable by myxoma virus while other clones were not. To investigate whether myxoma virus tropism in other mouse cells was dependent on any particular receptors, we exploited primary mouse embryo fibroblasts (MEFs) from wild-type (WT) mice and various gene knock-outs.

Since IFNs play a key role in mounting anti-viral responses, we hypothesized that the restrictive phenotype was related to the "antiviral state" mediated by IFN. Disruption of the chain of events of the IFN system, neutralizing circulating IFN with antibodies or generating IFN receptor negative mice, or mice with deleted genes in the intracellular pathway of signal transmission, would severely compromise the host's resistance to the myxoma virus which typically does not infect normal mouse cells.

In order to test this hypothesis we needed to demonstrate if the non-infectivity of myxoma virus in the nonpermissive cells was due to the antiviral action of IFNs. Various MEF cell types having knock-outs of one or more proteins involved in intracellular IFN signaling response were tested for the effect of MV infection on the IFN pathway.

Figure 2:
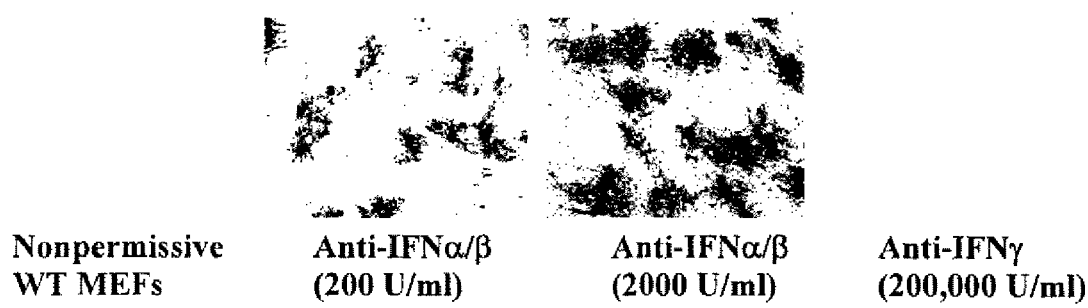
FIG. 2 is a phase contrast micrograph of nonpermissive WT murine embryonic fibroblasts ("MEFs") after exposure to Myxoma virus, demonstrating that the MEFs become permissive after inhibition of interferon α/β with neutralizing antibody.

Experiments performed on primary MEFs demonstrated that wildtype ("WT") MEFs are not infectable by myxoma virus. The MEFs are fully infectable by myxoma virus when the IFN pathway is blocked by neutralizing antibody to IFNα/β (FIG. 2). However, MEFs exposed to neutralizing antibodies to IFNγ remained nonpermissive. This outlined the importance of IFNα/β but not IFNγ in creating a permissive environment for myxoma virus to infect MEFs in vitro. Different intracellular signaling pathways for IFNα/β and IFNγ have been identified in the literature. However, both IFNα/β and IFNγ likely play an important role in infected hosts, unlike cultured fibroblasts. We predict that human tumors deficient in either IFNα/β and/or IFNγ pathway will be susceptible to myxoma virus infection in vivo.

Figure 4:
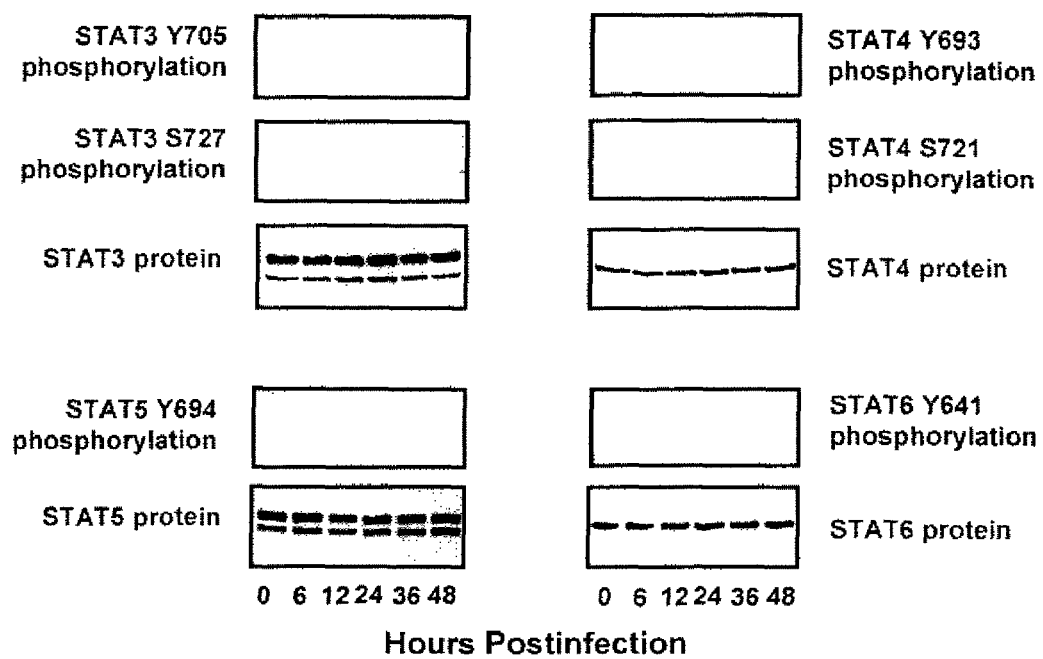
FIG. 4 is a Western blot showing phosphorylation states (inactivation) of STAT3, STAT4, STAT5 and STAT6 after Myxoma virus infection, demonstrating that nonpermissive infections of MEF cells does not activate any of these species.
Figure 3:
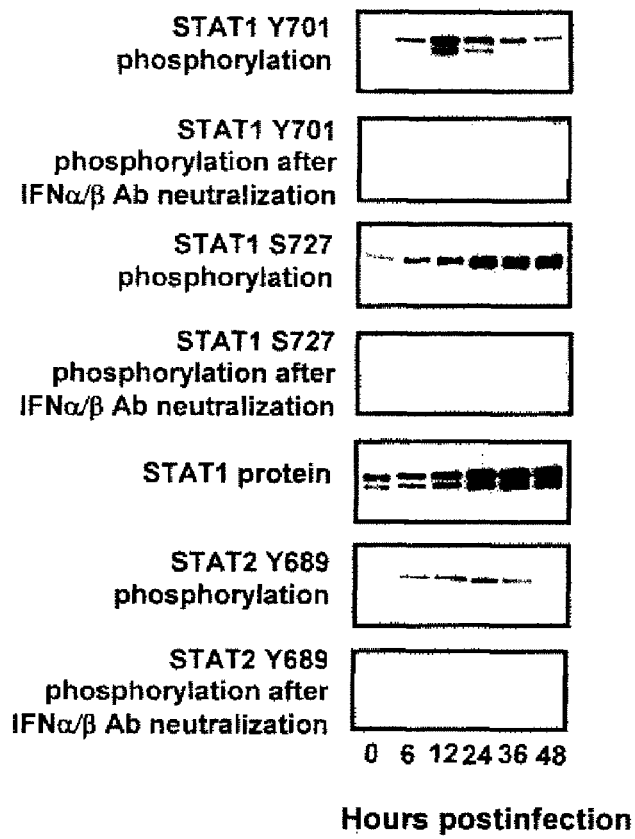
FIG. 3 is a Western blot showing phosphorylation states (activation) of STAT1 and STAT2 after Myxoma virus infection, demonstrating that nonpermissive infections of MEF cells is associated with activation of STAT 1 and STAT 2.

We examined the activity of STAT1 and STAT2 in nonpermissive WT MEFs that were infected with MV. The results shown in FIG. 3 indicated that STAT1 and STAT2 were activated. Further study showed that STAT3, STAT4 and STAT5 are not activated (FIG. 4).

Figure 5:
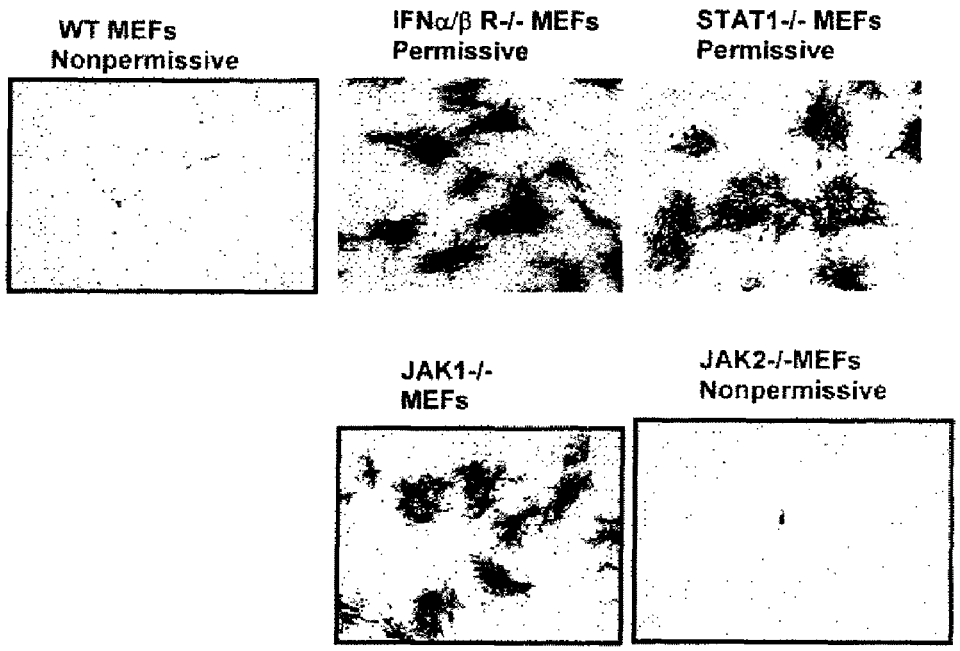
FIG. 5 is a phase contrast micrograph of IFNα/β R−/− MEFs and STAT1−/− MEFs, IFNα/β R−/− MEFs and STAT1−/− MEFs after infection with Myxoma virus, showing that inactivation of IFN/STAT/JAK signalling renders cells permissive for myxoma infection.

In order to confirm the importance of the IFNα/β intracellular pathway in maintaining a nonpermissive state in MEFs, genetic deletion studies were performed to provide disruptions in the IFNα/β receptors and in the intracellular cascade. Genetic deletion of IFN receptors or JAK1 or STAT1 was performed. MV was used to infect WT MEFs, IFNα/β R−/− MEFs and STAT1−/− MEFs. IFNα/β R−/− MEFs and STAT1−/− MEFs were permissive to MV demonstrating the IFNα/β and STAT1 signalling cascades are critical for MV infection (FIG. 5).

Figure 6:
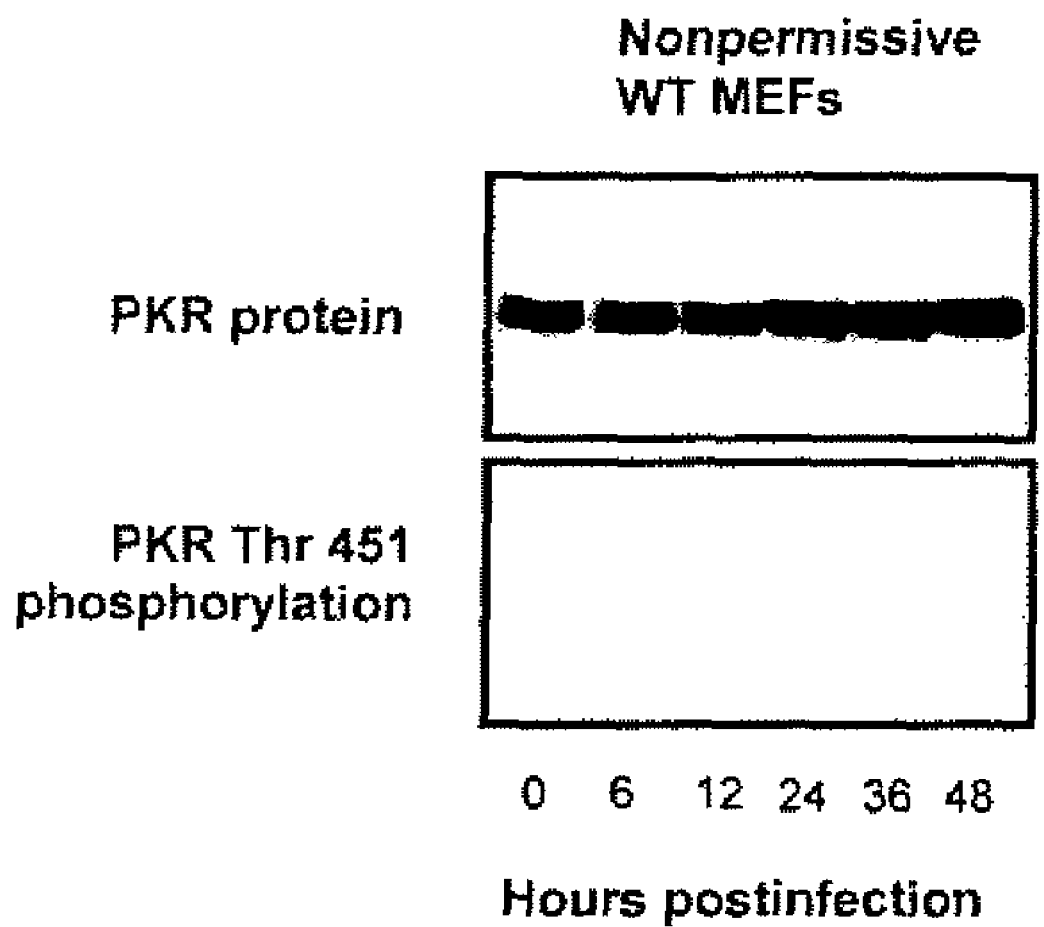
FIG. 6 is a Western blot showing phosphorylation states of PKR in nonpermissive wildtype MEFs after Myxoma virus infection, demonstrating that PKR is not activated by myxoma virus infection.
Figure 7:
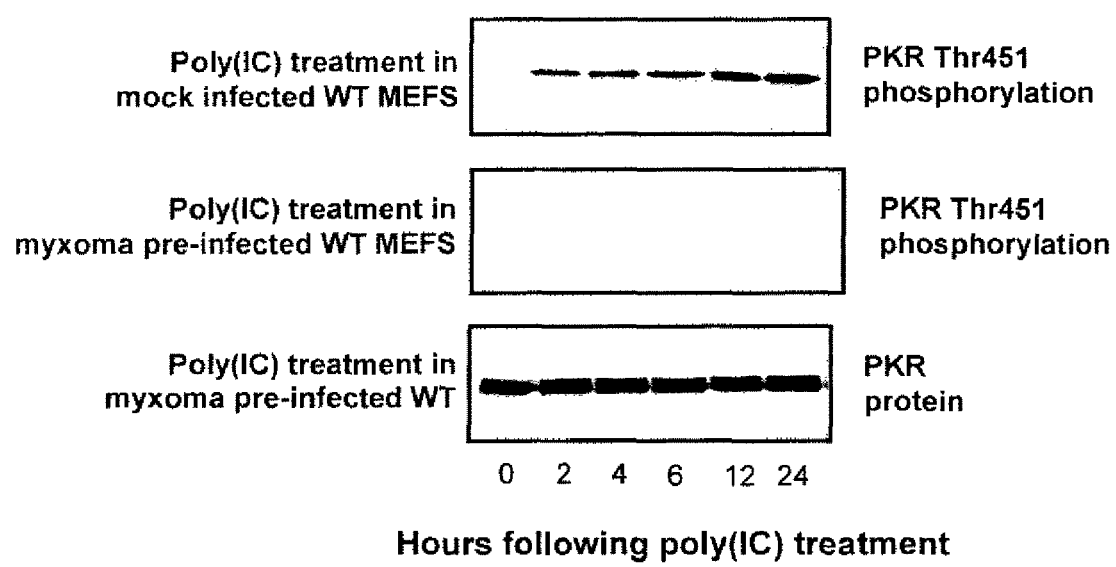
FIG. 7 is a Western blot showing phosphorylation states of PKR in wildtype MEFs either mock infected or pre-infected with Myxoma virus, showing that myxoma virus blocks PKR activation in MEF cells.
Figure 8:
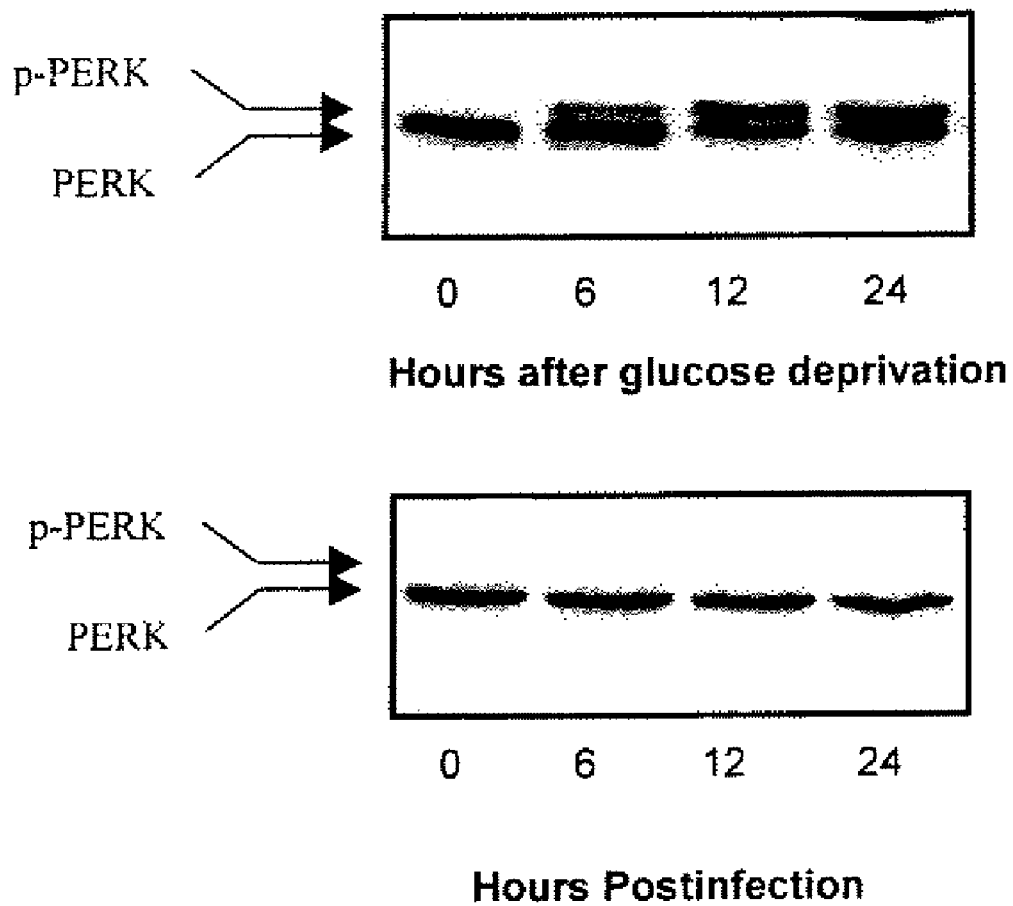
FIG. 8 is a Western blot showing phosphorylation states of PERK in wildtype MEFs after Myxoma virus infection, demonstrating that Myxoma virus blocks PERK activation in MEF cells.

Protein Kinase R (PKR) is an enzyme induced in a wide variety of cells by IFNα/β. This kinase, in the presence of dsRNA, undergoes autophosphorylation and then phosphorylates several cellular proteins including eukaryotic protein synthesis initiation factor (eIF-2α) whose phosphorylation can induces an inhibition of protein translation and apoptosis. PKR is also indicated in the activation of RNaseL. We examined the activation of PKR in nonpermissive MEFs following MV infection. PKR is not phosphorylated in nonpermissive MEFs in which the antiviral state is well established (FIG. 6). Furthermore MV infection inhibits PKR phosphorylation (FIG. 7). In addition, PERK (PRK-like, ER kinase) is not phosphorylated in the primary WT MEFs following myxoma virus infection (FIG. 8).

Figure 9:
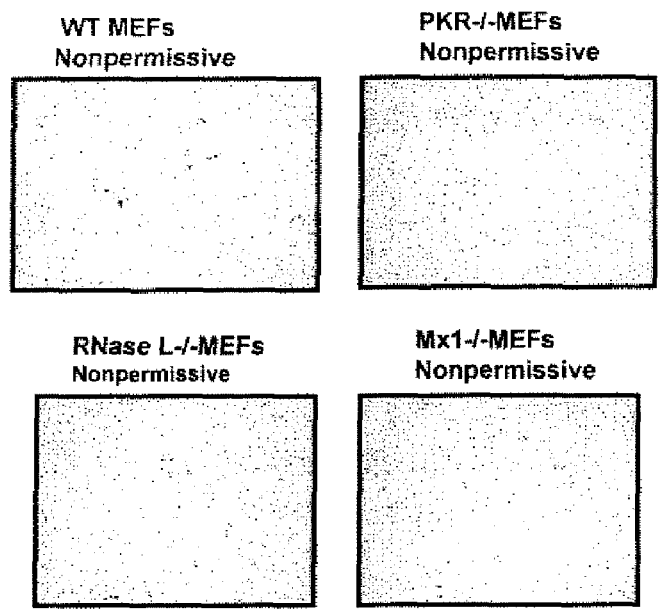
FIG. 9 is a phase contrast micrograph of PKR−/−, RNase L−/− and Mx1−/− triple knockout after exposure to Myxoma virus, showing that the antiviral state in MEF cells is mediated by a distinct pathway.
Figure 10:
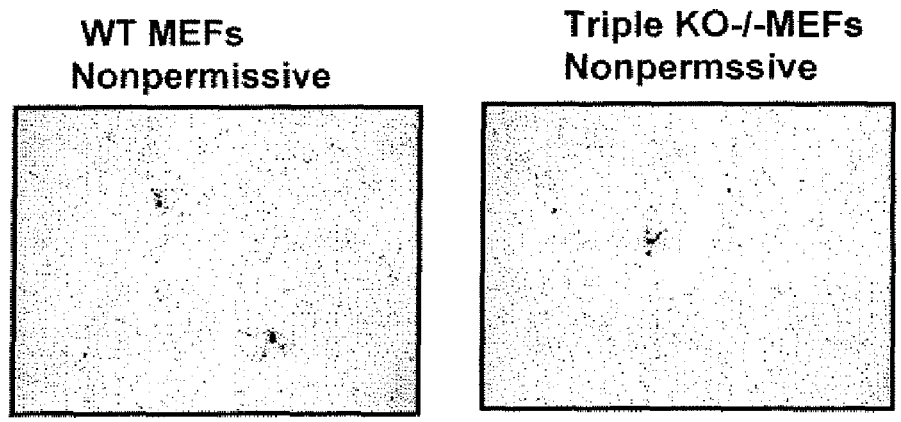
FIG. 10 is a phase contrast micrograph of PKR−/−, RNase L−/− and Mx1−/− triple knockout after exposure to Myxoma virus.
Figure 11:
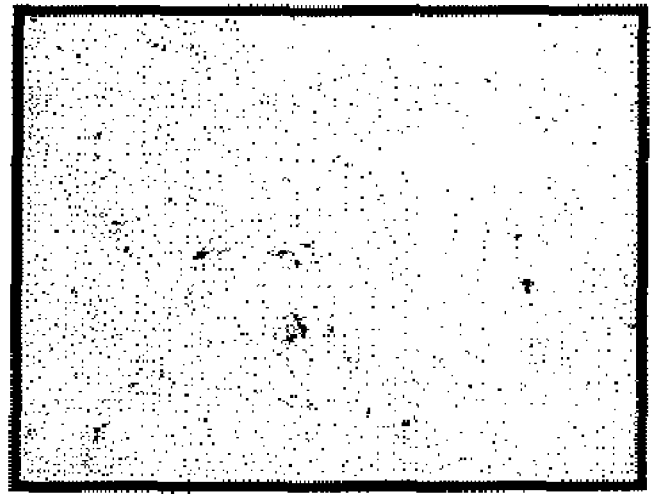
FIG. 11 is a phase contrast micrograph of PKR−/−, RNase L−/− and Mx1−/− triple knockout after treatment with neutralizing antibody to IFNα/β and after exposure to Myxoma virus.
Figure 11:
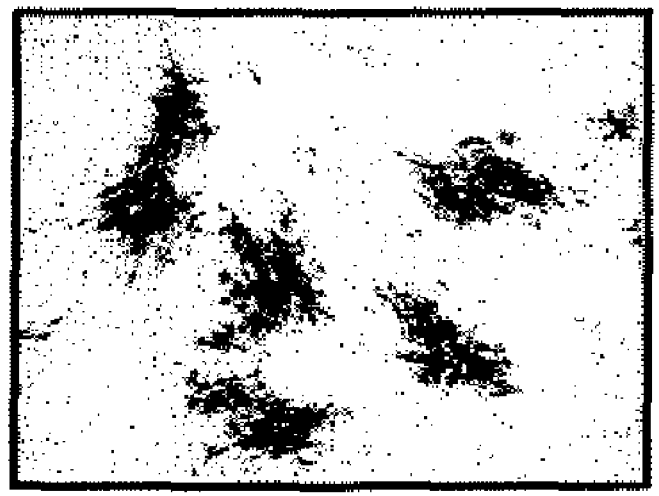

MV was use to infect MEFs with single gene knockouts of PKR, RNaseL or Mx1 (FIG. 9). It was discovered that PKR, RNaseL and Mx1 are nonessential for maintaining nonpermissiveness for myxoma virus infection. To further confirm the nonessential role of PKR, RNaseL and Mx1 a Triple knockout of PKR−/−, RNase L−/− and Mx1−/− in MEFs was performed. A PKR−/−, RNase L−/− and Mx1−/− triple knockout does not support myxoma virus infection (FIG. 10), however MEFs with a triple KO of PKR, RNaseL and Mx1 treated with a neutralizing antibody to Interferon α/β becomes permissive to myxoma virus infection (compare FIGS. 10 and 11). These experiments demonstrate that PKR, RNaseL and Mx1 are not essential in mediating the nonpermissiveness of MEFs to MV.

Figure 12:
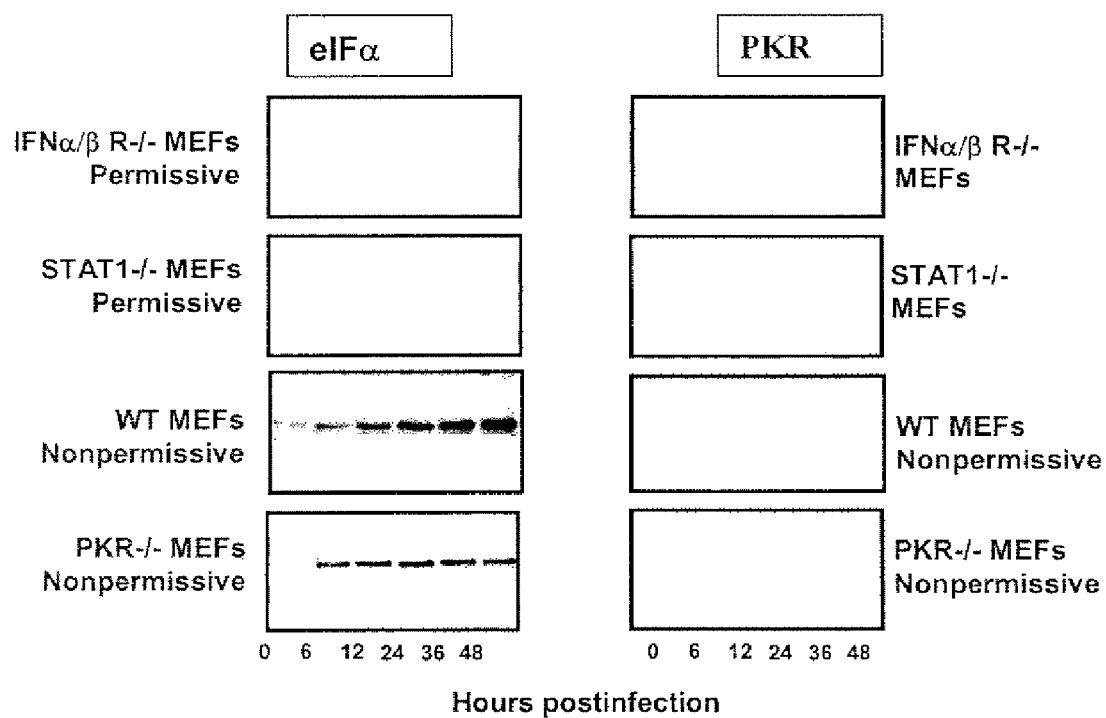
FIG. 12 is a Western blot showing phosphorylation levels of eIF2α and PKR in nonpermissive MEFs after treatment with neutralizing antibody to IFNα/β and after exposure to Myxoma virus, showing that eIF2α phosphorylation in nonresponsive cells is catalysed by a PKR-independent pathway.

Further studies were performed to examine the activation of eIF-2α and PKR in nonpermissive wildtype MEFs and permissive IFNα/β R−/− MEFs and STAT1−/− MEFs after MV infection. After MV infection, eIF-2α is phosphorylated in nonpermissive and permissive MEFs although PKR is not phosphorylated in either case (FIG. 12). This demonstrates that without the involvement of PKR and PERK, the antiviral state is mediated by another pathway that causes eIF2α phosphorylation.

Figure 13:
FIG. 13 is a Western blot showing STAT1 phosphorylation states in PKR−/−, RNase L−/− and Mx1−/− triple knockout after Myxoma virus infection, indicating normal IFN-induced signalling responses
Figure 13:
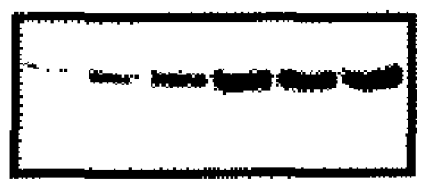
Figure 13:
Figure 14:
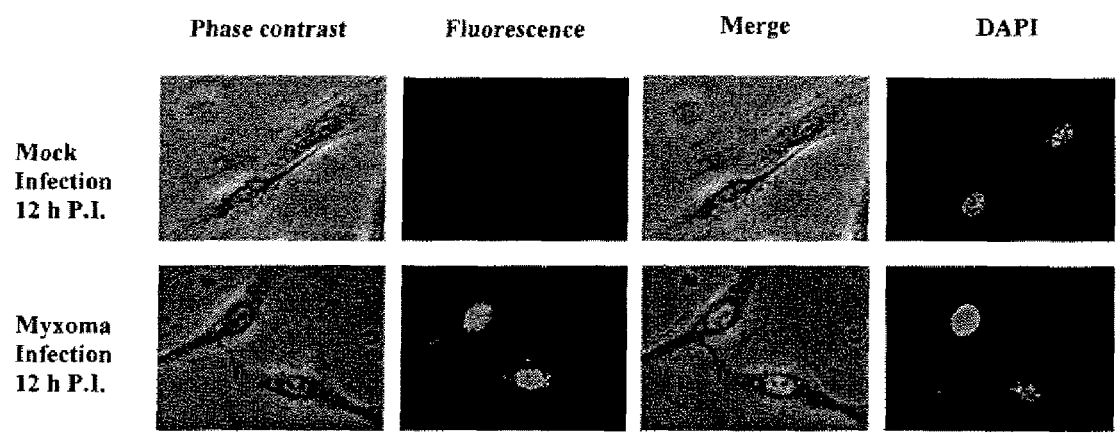
FIG. 14 is a phase contrast micrograph illustrating subcellular localization of tyrosine-phosphorylated STAT1 in nonpermissive PKR−/−+RNaseL−/−+Mx1−/− cells at 12 hours post-infection, indicating that the activated STAT localizes to the nucleus, as predicted for normal IFN/STAT signalling responses.

STAT1 is both serine- and tyrosine-phosphorylated following myxoma infections in nonpermissive PKR, RNaseL and Mx1 Triple KO MEFs (FIG. 13). Subcellular localization of tyrosine-phosphorylated STAT1 in nonpermissive PKR−/−+RNaseL−/−+Mx1−/− MEFs following myxoma virus infection is also shown (FIG. 14).

In summary, these results indicate that a parallel PKR/PERK-independent antiviral pathway involving IFN/STAT1 is critical for poxvirus tropism. Furthermore, eIF2α phosphorylation is the best marker for the antiviral action by INF.

Human Tumour Studies

Figure 15:
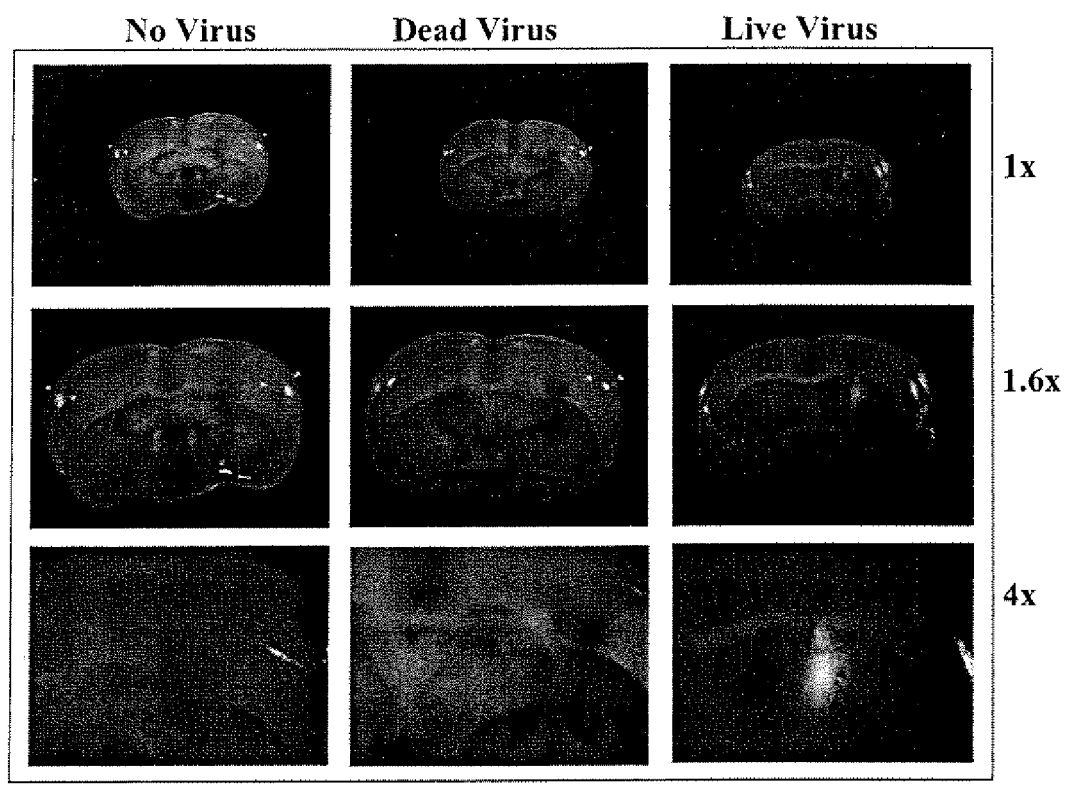
FIG. 15 is a fluorescent image of brains from nude mice having intracranial gliomas mock-infected or infected with dead or live Myxoma virus expressing GFP, showing targeting of myxoma to the glioma cells.
Figure 16:
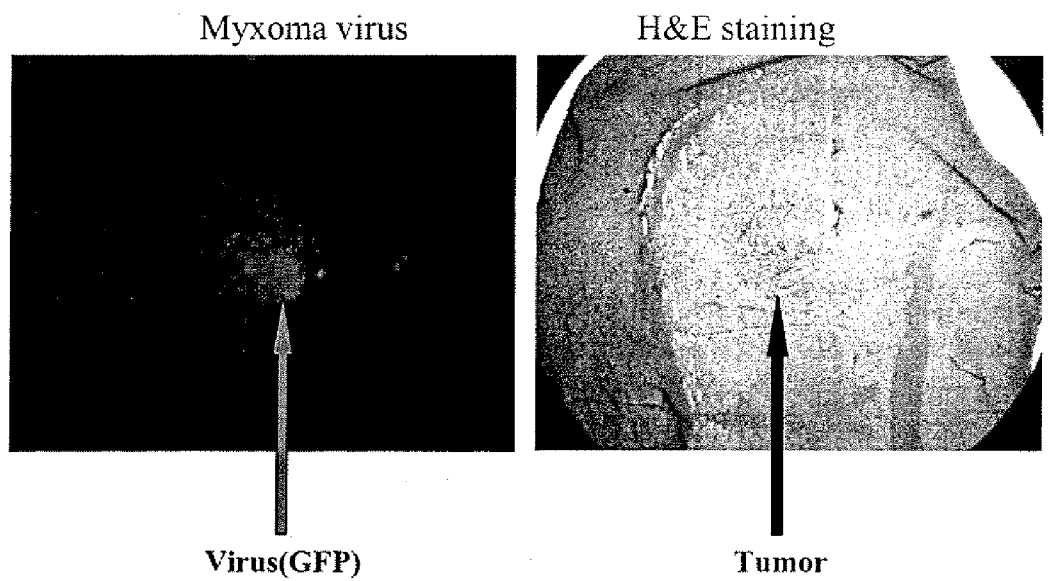
FIG. 16 is a fluorescent image and a photograph of a thin-sectioned mouse glioma infected with Myxoma virus expressing GFP showing that the myxoma virus replicated only in tumour cells.

We studied the ability of MV to infect human tumour cells in an in vivo system. Nude mice were injected with human glioma cells, and subsequently developed intracranial gliomas. Live virus was able to infect these human tumours cells but did not infect surrounding cells (FIG. 15). The localization of fluorescent signal from GFP to the tumour is depicted in FIG. 16.

Given that many human tumours are non-responsive to interferon, and that the tumour cells do not have normal IFN signaling cascades compared to those found in normal human cells, studies were performed to investigate the effect of myxoma virus on human tumours. The results are summarized below.

Figure 17:
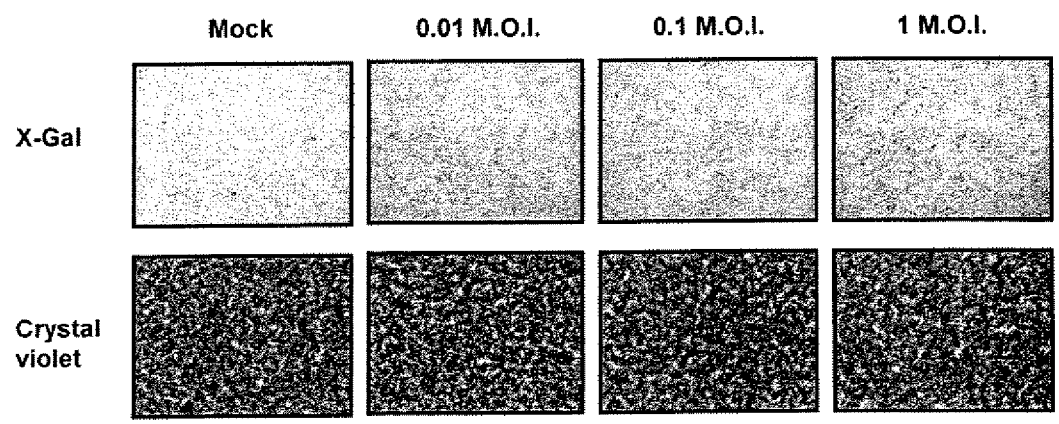
FIG. 17 is a phase contrast micrograph of HT29 human tumour cells, stained with either X-Gal or Crystal violet after infection with Myxoma virus, showing an example of a non-permissive infection in human cells.
Figure 18:
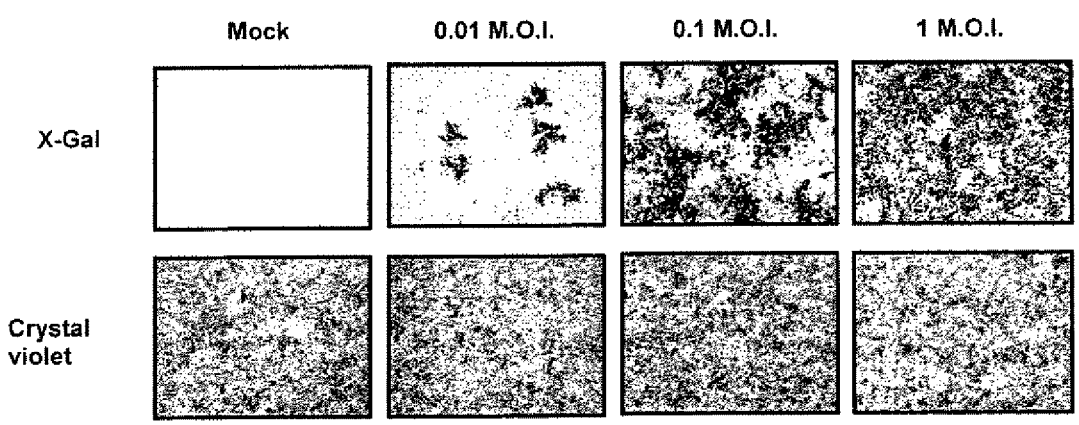
FIG. 18 is a phase contrast micrograph of HOP92 human tumour cells, stained with X-Gal or Crystal Violet after infection with Myxoma virus, showing an example of a permissive infection of human cells.
Figure 19:
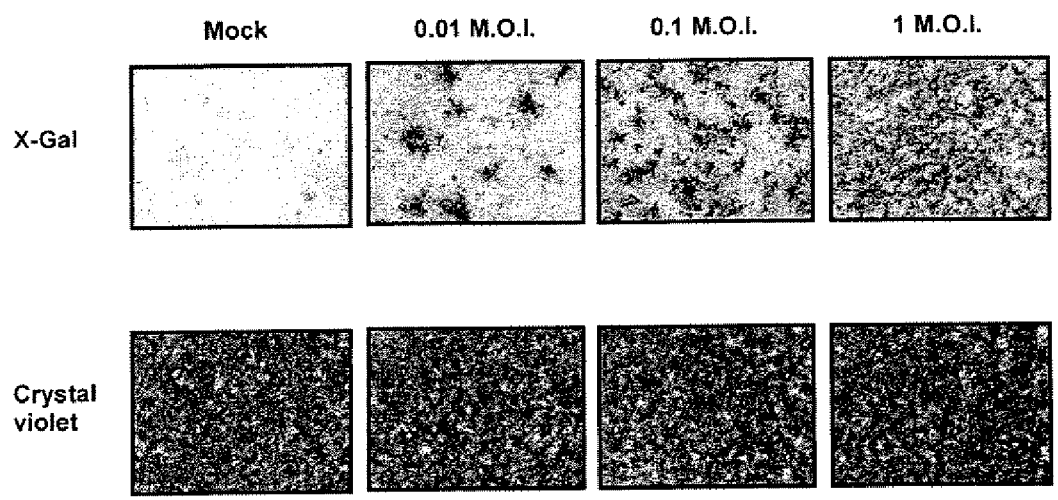
FIG. 19 is a phase contrast micrograph of OVCAR4 human tumour cells, stained with either X-Gal or Crystal Violet after infection with Myxoma virus, showing an example of a permissive infection of human cells.
Figure 20:
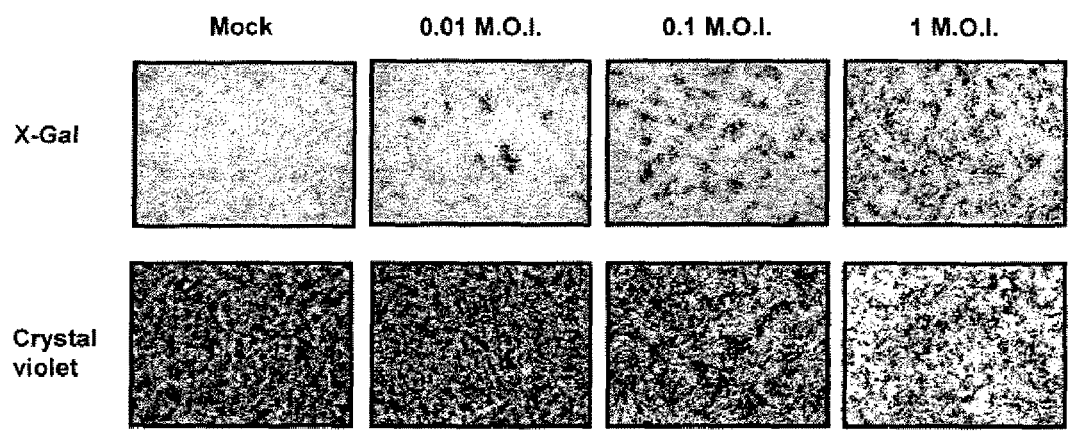
FIG. 20 is a phase contrast micrograph of SK-MEL3 human tumour cells, stained with either X-Gal or Crystal Violet after infection with Myxoma virus, showing an example of a permissive infection of human cells.
Figure 21:
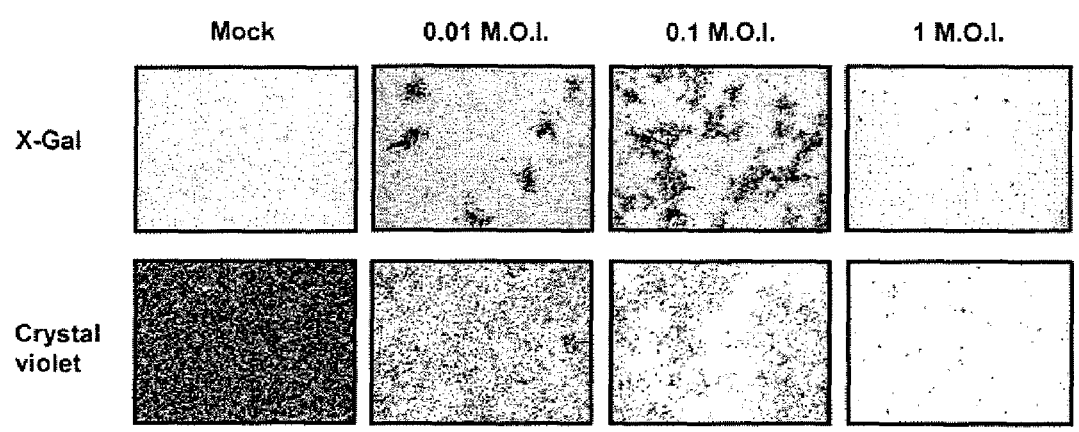
FIG. 21 is a phase contrast micrograph of SK-MEL28 human tumour cells, stained with either X-Gal or Crystal Violet after infection with Myxoma virus, showing an example of a semi-permissive infection of human tumour cells.
Figure 22:
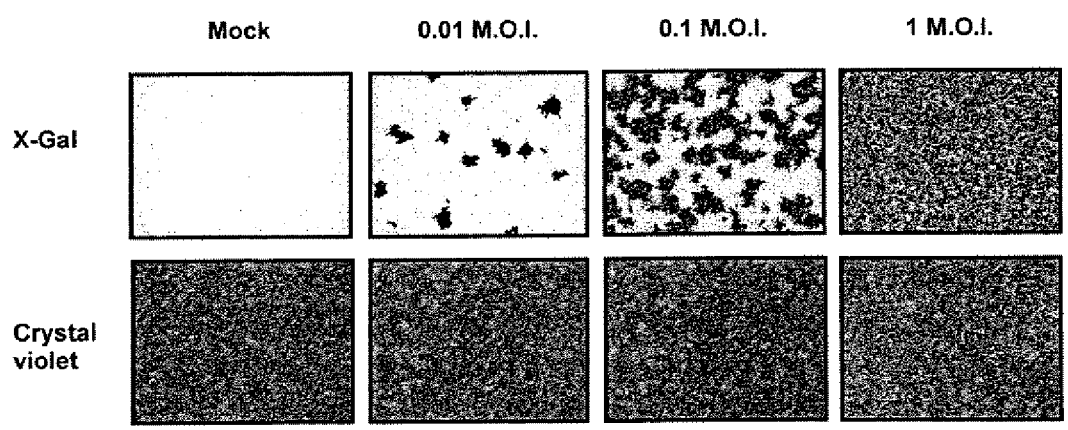
FIG. 22 is a phase contrast micrograph of BGMK cells, stained with either X-Gal or Crystal Violet after infection with Myxoma virus, showing a typical permissive control infection.

Initially, Myxoma virus was used to study the infectivity and cytolytic effects on various control and human tumour cell lines: BGMK, HT29, HOP92, OVCAR4, SK-MEL3, and SK-MEL28. MV demonstrated various infectivity and cytolytic results: HT29 (FIG. 17) HOP92 (FIG. 18), OVCAR4 (FIG. 19) SK-MEL3 (FIG. 20), SK-MEL28 (FIG. 21) and BGMK (FIG. 22).

Additional tumour cells were tested and Table 1 below classifies the various tumour types tested as nonpermissive, permissive or semi-permissive. Semi-permissive indicates Myxoma virus was moderately infectable as compared to permissive cell lines.

TABLE 1

Myxoma Virus Trophism for Human tumour cells

| Cell | Type | Nonpermissive | Permissive | Semi-Permissive |
|---|---|---|---|---|
| HT29 | Colon | X | | |
| HOP92 | Lung | | X | |
| M14 | Melanoma | | | X |
| SK-MEL3 | Melanoma | | | X |
| SK-MEL28 | Melanoma | | | X |
| OVCAR4 | Ovarian | | X | |
| OVCAR5 | Ovarian | X | | |
| SKOV3 | Ovarian | | | X |
| PC3 | Prostate | | X | |
| DU145 | Prostate | X | | |
| CAKI-1 | Renal | | X | |
| 786-0 | Renal | | X | |
| T47D | Breast | X | | |
| MDAMB 435 | Breast | X | | |

Figure 23:
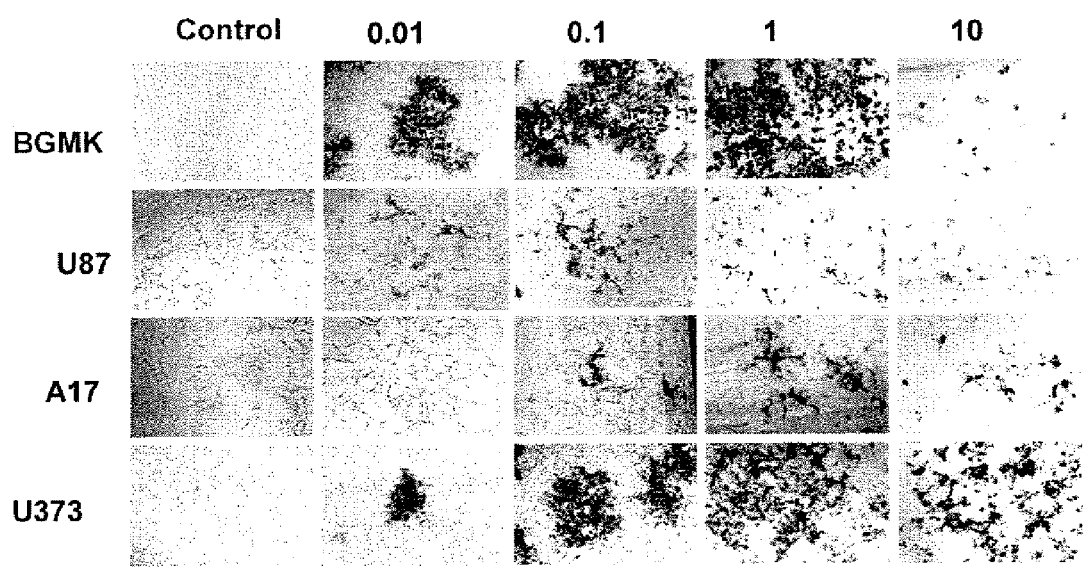
FIG. 23 is a phase contrast micrograph of positive control BGMK cells and human tumour lines U87, A172 and U373 infected with increasing concentrations of Myxoma virus expressing the LacZ protein, stained with X-Gal, showing that these human glioma cells were all permissive for myxoma virus replication.
Figure 24:
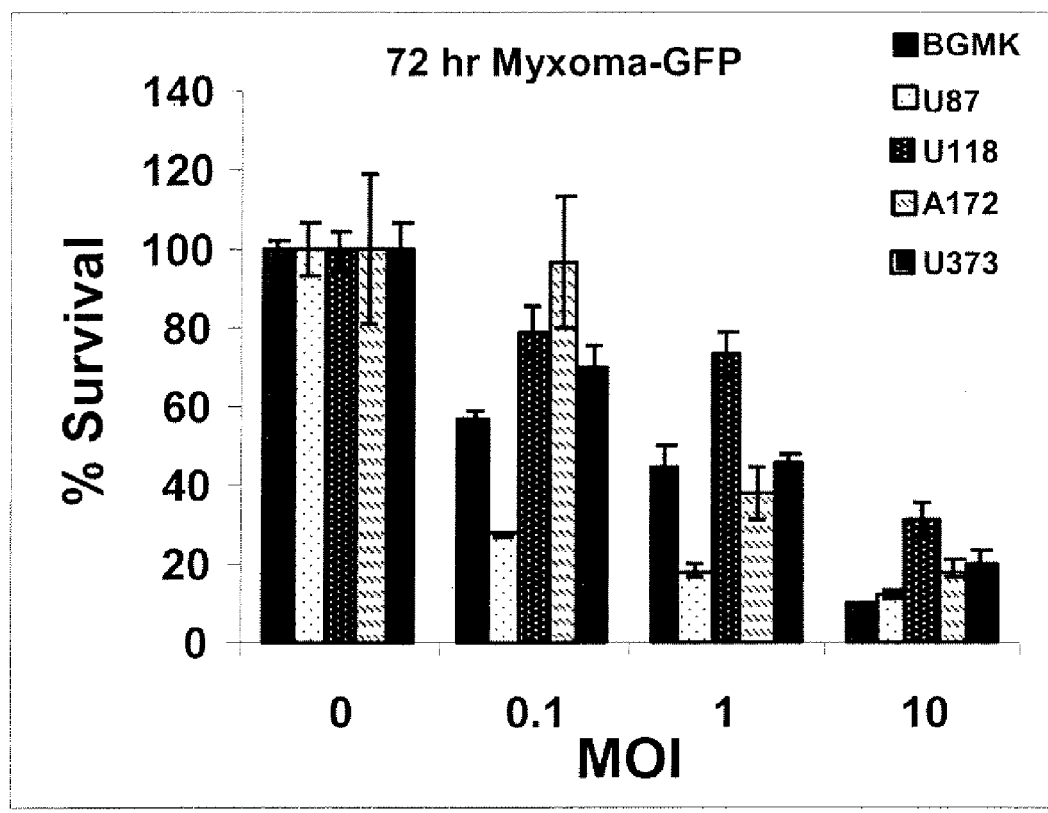
FIG. 24 is a graph depicting survival rate of BGMK, U87, A172 and U373 cells infected with Myxoma virus, 72 hours post-infection, at increasing concentrations of the virus, demonstrating the ability of myxoma to kill all of these cells.
Figure 25:
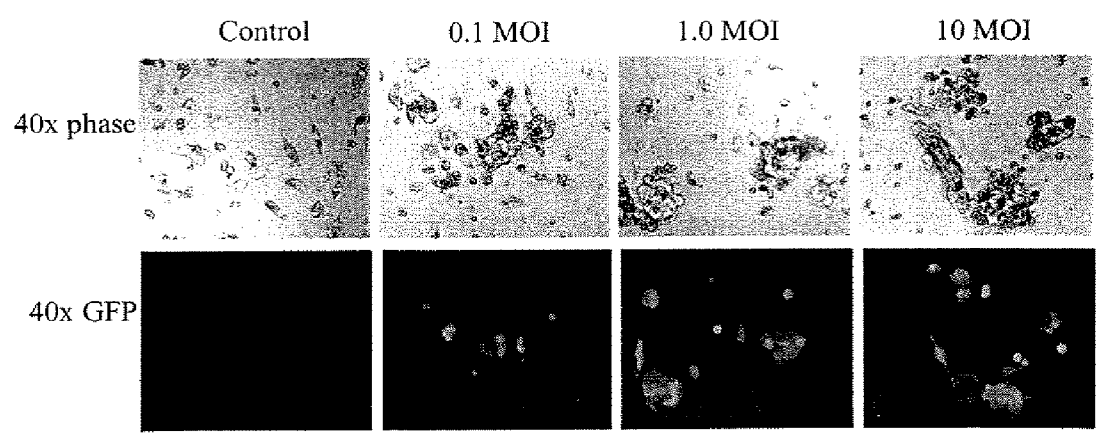
FIG. 25 is a phase contrast micrograph and fluorescence micrograph of SF04 1585 astrocytoma cells infected with MV GFP, showing the infection in primary human glioma cells.
Figure 26:
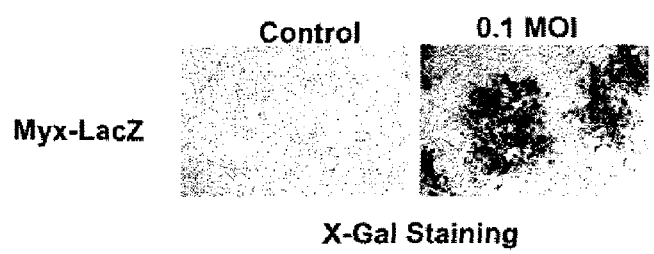
FIG. 26 is a phase contrast micrograph of U373 glioma cells infected with Myxoma virus expressing the LacZ protein and stained with X-Gal, showing infection of these human tumour cells.
Figure 27:
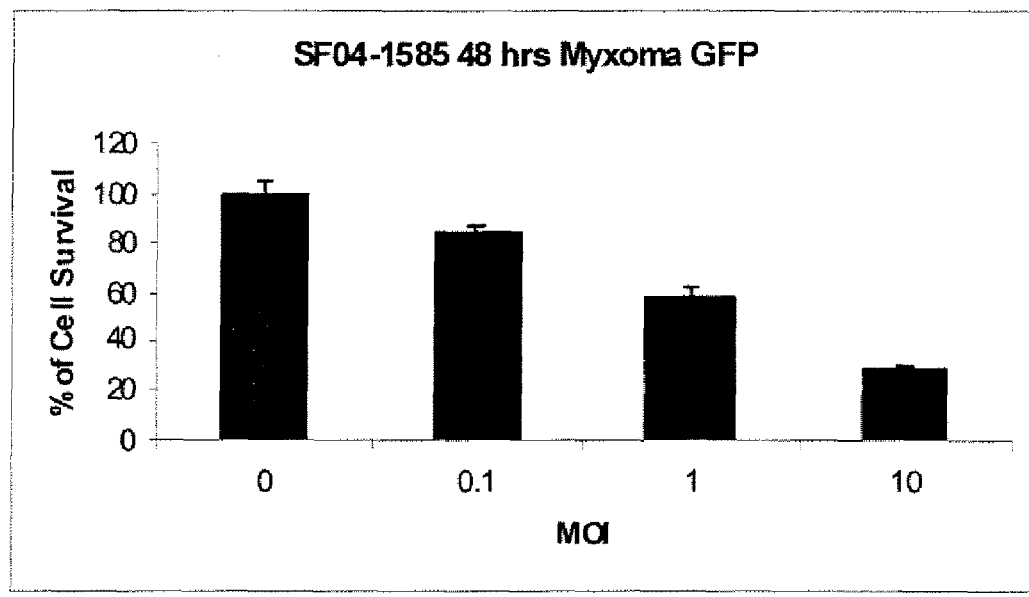
FIG. 27 is a graph depicting the survival rate of SF04 1585 cells infected with MV GFP 48 hours post-infection, showing killing of these infected human tumour cells.
Figure 28:
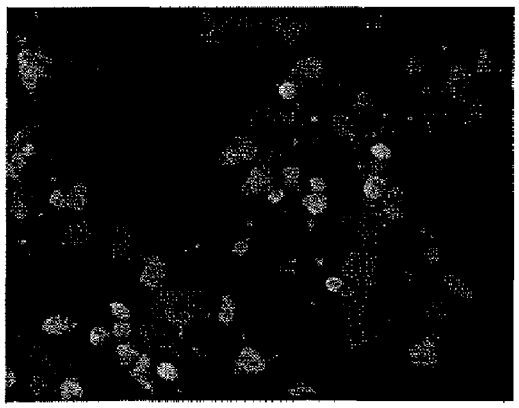
FIG. 28 is a fluorescence micrograph of Daoy and D384 medulloblastoma lines infected with Myxoma virus expressing GFP, showing infection of these human tumour cells.
Figure 28:
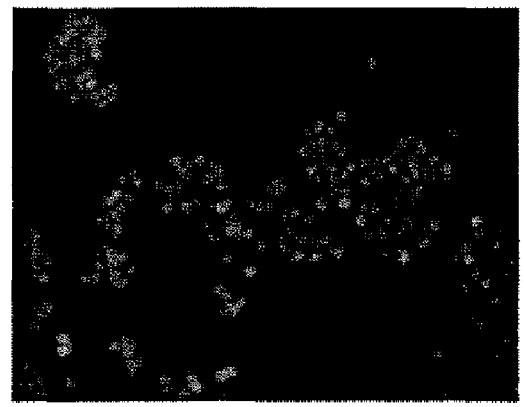

Various human tumour lines demonstrated varying responsiveness to infection with increasing concentrations of MV-LacZ. For example, U373 cells required higher virus titres to achieve the levels of cell killing achieved with lower virus titres in U87 (FIG. 23 and FIG. 24). Myxoma efficiently infected astrocytoma cells (FIG. 25), and glioma cells (FIG. 26). Myxoma was effective at 48 hours post-infection at killing human astrocytoma and pediatric medulloblastoma cells (FIGS. 27 and 28).

As can be understood by one skilled in the art, many modifications to the exemplary embodiments described herein are possible. The invention, rather, is intended to encompass all such modification within its scope, as defined by the claims.

What is claimed is:

1. A method for inhibiting a cell that has a deficient innate anti-viral response comprising administering to the cell an effective amount of Myxoma virus, wherein the cell is a human cell chronically infected with a virus.

2. The method of claim 1, wherein the Myxoma virus is a wild-type virus.

3. The method of claim 1, wherein the Myxoma virus is genetically modified.

4. The method of claim 3, wherein the Myxoma virus is genetically modified to express a therapeutic gene.

5. The method of claim 1, wherein the virus is administered systemically.

6. The method of claim 1, wherein less than $10^9$ pfu of the virus are administered.

7. The method of claim 1, wherein between about $10^2$ and $10^9$ pfu of the virus are administered.

8. A method for treating a disease state characterized by the presence of cells that have a deficient innate anti-viral response, comprising administering to a human patient in need thereof an effective amount of Myxoma virus, wherein the disease state is a chronic viral infection and wherein the Myxoma virus inhibits the cells.

9. The method of claim 8, wherein the Myxoma virus is a wild-type virus.

10. The method of claim 8, wherein the Myxoma virus is genetically modified.

11. The method of claim 10, wherein the Myxoma virus is genetically modified to express a therapeutic gene.

12. The method of claim 8, wherein the virus is administered systemically.

13. The method of claim 8, wherein less than $10^9$ pfu of the virus are administered.

14. The method of claim 8, wherein between about $10^2$ and $10^9$ pfu of the virus are administered.

15. A kit comprising Myxoma virus and instructions for treating a chronic viral infection in a patient in need thereof.

* * * * *